US012749589B2

(12) United States Patent
Regna et al.

(10) Patent No.: US 12,749,589 B2
(45) **Date of Patent: *Sep. 29, 2026**

(54) PURIFICATION PROCESS FOR THE PREPARATION OF NON-CARRIER ADDED COPPER-64

(71) Applicant: Curium US LLC, St. Louis, MO (US)

(72) Inventors: Brian Regna, St. Louis, MO (US); Allan Casciola, St. Louis, MO (US); Lauren Radford, St. Louis, MO (US); Shaun Loveless, St. Louis, MO (US); David Pipes, St. Louis, MO (US); William Uhland, St. Louis, MO (US); Craig Brunkhorst, St. Louis, MO (US)

(73) Assignee: Curium US LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/195,850

(22) Filed: May 1, 2025

(65) Prior Publication Data

US 2025/0273354 A1 Aug. 28, 2025

Related U.S. Application Data

(63) Continuation of application No. 18/745,896, filed on Jun. 17, 2024, now Pat. No. 12,315,649, which is a continuation-in-part of application No. 18/238,951, filed on Aug. 28, 2023, now Pat. No. 12,148,542, which is a continuation of application No. 17/993,186, filed on Nov. 23, 2022, now Pat. No. 11,798,701, which is a continuation of application No. 17/894,874, filed on Aug. 24, 2022, now Pat. No. 11,581,103, which is a continuation of application No. 17/466,443, filed on Sep. 3, 2021, now Pat. No. 11,521,762.

(60) Provisional application No. 63/654,662, filed on May 31, 2024, provisional application No. 63/074,356, filed on Sep. 3, 2020.

(51) Int. Cl.

| | |
|---|---|
| ***G21G 1/10*** | (2006.01) |
| ***A61K 51/04*** | (2006.01) |
| ***C01G 3/00*** | (2006.01) |
| ***G21G 1/00*** | (2006.01) |
| ***G21G 4/08*** | (2006.01) |

(52) U.S. Cl.

CPC ......... *G21G 1/001* (2013.01); *A61K 51/0482* (2013.01); *C01G 3/003* (2013.01); *G21G 1/10* (2013.01); *G21G 4/08* (2013.01); *G21G 2001/0094* (2013.01)

(58) Field of Classification Search

CPC ............. G21G 1/00; G21G 4/08; A61K 51/04

See application file for complete search history.

(56) References Cited

U.S. PATENT DOCUMENTS

| | | | | |
|---|---|---|---|---|
| 5,619,545 | A | 4/1997 | Grummon et al. | |
| 6,011,825 | A * | 1/2000 | Welch | G21G 1/10 376/195 |
| 8,647,595 | B2 | 2/2014 | Watanabe et al. | |
| 11,521,762 | B2 | 12/2022 | Pipes et al. | |
| 11,581,103 | B2 | 2/2023 | Pipes et al. | |
| 11,798,701 | B2 | 10/2023 | Pipes et al. | |
| 11,972,874 | B2 | 4/2024 | Pipes et al. | |
| 11,978,569 | B2 | 5/2024 | Pipes et al. | |
| 2006/0004491 | A1 | 1/2006 | Welch et al. | |
| 2022/0118120 | A1 | 4/2022 | Wurzer et al. | |
| 2023/0165979 | A1 | 6/2023 | Babich et al. | |
| 2023/0402199 | A1 | 12/2023 | Pipes et al. | |
| 2023/0420152 | A1 | 12/2023 | Pipes et al. | |
| 2024/0024519 | A1 | 1/2024 | Donovan et al. | |
| 2024/0331889 | A1 | 10/2024 | Pipes et al. | |
| 2024/0339235 | A1 | 10/2024 | Regna et al. | |

FOREIGN PATENT DOCUMENTS

| | | | |
|---|---|---|---|
| CN | 1522448 | A | 8/2004 |
| CN | 111133842 | A | 5/2020 |
| JP | 2007512118 | A | 5/2007 |
| JP | 2013113821 | A | 6/2013 |
| JP | 5880931 | B2 | 3/2016 |
| KR | 20100085727 | A | 7/2010 |
| KR | 101041180 | B1 | 6/2011 |
| KR | 101041181 | B1 | 6/2011 |
| KR | 20230066382 | A | 5/2023 |
| TW | 201141791 | A | 12/2011 |
| WO | 2019203342 | A1 | 10/2019 |

OTHER PUBLICATIONS

Carolyn J Anderson et al., Production and Applications of Copper-64 Radiopharmaceuticals, Methods in Enzymology, 386, 237-261. (Year: 2004).*

A. Mushtaq et al. Production of low and high specific activity 64Cu in a reactor, J Radioanal Nucl Chem, 284, 265-271. (Year: 2010).*

Gaehle Grgory et al, Reproducible High Yielding Cu-64 Radioisotope Manufacturing, Washington University Office of Technology Management. (Year: 2019).*

Miguel A. Avila-Rodriguez et al., Simultaneous production of high specific activity 64Cu and 61Cu with 11.4 MeV protons on enriched 64Ni nuclei, Applied Radiation and Isotopes, 65, 1115-1121. (Year: 2007).*

(Continued)

*Primary Examiner* — Michael G. Hartley
*Assistant Examiner* — Jagadishwar R Samala
(74) *Attorney, Agent, or Firm* — Polsinelli PC

(57) ABSTRACT

Compositions comprising high levels of high specific activity copper-64, and process for preparing said compositions. The compositions comprise from about 2 Ci to about 15 Ci of copper-64 and have specific activities up to about 3800 mCi copper-64 per microgram of copper. The processes for preparing said compositions comprise bombarding a nickel-64 target with a low energy, high current proton beam, and purifying the copper-64 from other metals by a process comprising ion exchange chromatography or a process comprising a combination of extraction chromatography and ion exchange chromatography.

30 Claims, 5 Drawing Sheets

(56) References Cited

OTHER PUBLICATIONS

Alliot C., et al., "One Step Purification Process for No-Carrier-Added 64Cu Produced Using Enriched Nickel Target," Radiochimica Acta, 2011, vol. 99, pp. 627-630.
Anderson C. J., et al., "Production and Applications of Copper-64 Radiopharmaceuticals," Methods in Enzymology, 2004, vol. 386, pp. 237-261.
Anderson C. J., et al., "The In Vivo Behavior of Copper-64-Labeled Azamacrocyclic Complexes," Nuclear Medicine Biology, 1998, vol. 25, pp. 523-530.
Avila-Rodriguez M. A., et al., "Simultaneous Production of High Specific Activity 64Cu and 61Co with 11.4 MeV Protons on Enriched 64Ni Nuclei," Applied Radiation and Isotopes, 2007, vol. 65, pp. 1115-1120.
Braccini S., et al., "Science with a Medical PET Cyclotron," CERN Courier, Apr. 2016, pp. 21-22.
Burke P., et al., "An Automated Method for Regular Productions of Copper-64 for PET Radiopharmaceuticals," Inorganica Chimica Acta, 2010, vol. 363, No. 6, pp. 1316-1319.
Chakarvarty R., et al., "A Simple and Robust Method for Radiochemical Separation of No-Carrier-Added 64Cu Produced in a Research Reactor for Radiopharmaceutical Preparation," Applied Radiation and Isotopes, Nov. 2020, vol. 165, 7 pages.
Corrected Notice of Allowance for U.S. Appl. No. 18/238,951, dated Aug. 1, 2024, 2 pages.
Corrected Notice of Allowance for U.S. Appl. No. 18/745,906, dated Dec. 27, 2024, 2 pages.
Extended European Search Report for European Application No. 21865183.4, dated Nov. 21, 2024, 13 Pages.
Fan X., et al., "A simple and selective method for the separation of Cu radioisotopes from Nickel," Nuclear Medicine and Biology, 2006, vol. 33, pp. 939-944.
Final Office Action for U.S. Appl. No. 17/466,443, dated May 24, 2022, 15 pages.
Final Office Action for U.S. Appl. No. 18/745,896, dated Jan. 8, 2025, 13 Pages.
Final Office Action for U.S. Appl. No. 18/238,972, dated Apr. 9, 2024, 8 pages.
Final Office Action for U.S. Appl. No. 18/733,537, dated Dec. 26, 2024, 13 pages.
Final Office Action for U.S. Appl. No. 18/733,537, dated Jan. 21, 2025, 15 pages.
Gaehle G., et al., "Reproducible High Yielding Cu-64 Radioisotope Manufacturing," Washington University Office of Technology Management, Oct. 2019, 3 pages.
Ikotun O. F., et al., "The Rise of Metal Radionuclides in Medical Imaging: Copper-64, Zirconium-89 and Yttrium-86," Future Medicine Chemistry, 2011, vol. 3, No. 5, pp. 599-621, [doi:10.4155/fmc.11.14].
International Search Report and Written Opinion for PCT Application No. PCT/US2024/060406, dated Apr. 2, 2025, 20 pages.
International Search Report and Written Opinion for PCT/US2021/049039, dated Jan. 21, 2022, 12 pages.
Jeffery C. M., et al., "Routine Production of Copper-64 Using 11.7 MeV Protons," AIP Conference Proceedings, 2012, vol. 1509, pp. 84-90.
Kraus K. A., et al., "Proceedings of the International Conference on the Peaceful Uses of Atomic Energy," United Nations Publication, 1956, vol. 7, 15 pages.
Kume M., et al., "A Semi-Automated System for the Routine Production of Copper-64," Applied Radiation and Isotopes, Aug. 2012, vol. 70, No. 1, pp. 1803-1806.
Matarrese M., et al., "Automated Production of Copper Radioisotopes and Preparation of High Specific Activity [64Cu]Cu-ATSM for PET Studies," Applied Radiation and Isotopes, 2010, vol. 68, No. 1, pp. 5-13.
McCarthy D. W., et al., "Efficient Production of High Specific Activity 64Cu Using a Biomedical Cyclotron," Nuclear Medicine Biology, 1987, vol. 24, pp. 35-43.
Mikolajczak R., et al., "Radiometals for Imaging and Theranostics, Current Production, and Future Perspectives," Journal of Labelled Compounds and Radiopharmaceuticals, 2019, vol. 62, pp. 615-634.
Non-Final Office Action for U.S. Appl. No. 18/238,951, dated Feb. 23, 2024, 25 pages.
Non-Final Office Action for U.S. Appl. No. 18/745,896, dated Sep. 5, 2024, 15 Pages.
Non-Final Office Action for U.S. Appl. No. 17/466,443, dated Mar. 29, 2022, 28 pages.
Non-Final Office Action for U.S. Appl. No. 17/993,186, dated Apr. 27, 2023, 25 pages.
Non-Final Office Action for U.S. Appl. No. 18/213,194, dated Nov. 9, 2023, 27 pages.
Non-Final Office Action for U.S. Appl. No. 18/238,966, dated Dec. 6, 2023, 33 pages.
Non-Final Office Action for U.S. Appl. No. 18/238,972, dated Dec. 14, 2023, 13 pages.
Non-Final Office Action for U.S. Appl. No. 18/238,972, dated May 16, 2024, 24 pages.
Non-Final Office Action for U.S. Appl. No. 18/733,537, dated Aug. 22, 2024, 15 pages.
Notice of Allowance for U.S. Appl. No. 17/894,874, dated Nov. 9, 2022, 29 pages.
Notice of Allowance for U.S. Appl. No. 18/745,896, dated Mar. 26, 2025, 9 Pages.
Notice of Allowance for U.S. Appl. No. 17/993,186, dated Aug. 24, 2023, 16 pages.
Notice of Allowance for U.S. Appl. No. 18/213,194, dated Mar. 13, 2024, 33 pages.
Notice of Allowance for U.S. Appl. No. 18/238,951, dated Sep. 25, 2024, 2 pages.
Notice of Allowance for U.S. Appl. No. 18/238,966, dated Mar. 27, 2024, 9 pages.
Notice of Allowance for U.S. Appl. No. 18/745,906, dated Oct. 17, 2024, 10 pages.
Notice of Allowance in related U.S. Appl. No. 17/466,443, dated Aug. 31, 2022, 10 pages.
Notice of Allowance in related U.S. Appl. No. 18/238,951, dated Jul. 17, 2024, 10 pages.
Obata A., et al., "Production of Therapeutic Quantities of 64Cu Using a 12 MeV Cyclotron," Nuclear medicine and biology, 2003, vol. 30, No. 5, pp. 535-539, doi:10-1016/S0969-8051(03)00024-6.
Office Action for Japanese Patent Application No. 2023-514725, mailed Apr. 2, 2025, 7 Pages.
Partial Supplementary Search Report for European Application No. 21865183.4, dated Aug. 9, 2024, 12 pages.
Smith S. V., et al., "Separation of 64Cu from 67Ga Waste Products Using Anion Exchange and Low Acid Aqueous/Organic Mixtures," Radiochimica Acta, 1996, vol. 75, pp. 65-68.
Szajek L. P., et al., "Semi-Remote Production of [64Cu]CuCl2 and Preparation of High Specific Activity [64Cu]Cu-ATSM for PET Studies," Radiochimica Acta, 2005, vol. 93, pp. 239-244.
Thieme S., et al., "Module-Assisted Preparation of 64 Cu with High Specific Activity," Applied Radiation and Isotopes, Apr. 2012, vol. 70, No. 4, pp. 602-608.
Non-Final Office Action for U.S. Appl. No. 19/030,236, dated Oct. 1, 2025, 14 pages.
Non-Final Office Action for U.S. Appl. No. 19/242,810, dated Sep. 5, 2025, 6 pages.
Notice of Allowance for U.S. Appl. No. 19/184,830, dated Jul. 15, 2025, 9 pages.
Notice of Allowance for U.S. Appl. No. 18/733,537, dated Aug. 19, 2025, 11 pages.
Toyota T., et al., "A purification system for 64Cu produced by a biomedical cyclotron for antibody PET imaging," Journal of Radioanal Nuclear Chemistry, 2013, vol. 298, pp. 295-300.
Xie Q., et al., "Establishing Reliable Cu-64 Production Process: From Target Plating to Molecular Specific Tumor Micro-PET Imaging," Molecules, 2017, vol. 22, No. 641, pp. 10 pages.
Zweit J., et al., "Excitation Functions for Deuteron Induced Reactions in Natural Nickel: Production of No-Carrier-Added 64Cu from Enriched 64Ni Targets for Positron Emission Tomography," Inter-

(56) References Cited

OTHER PUBLICATIONS national Journal of Radiation Applications and Instrumentation: Part A, 1991, vol. 42, No. 2, pp. 193-197.
Office Action for Japanese Patent Application No. 2023-514725, mailed Jul. 10, 2025, 3 Pages.
Final Office Action for U.S. Appl. No. 19/030,236, dated Feb. 19, 2026, 7 pages.
International Search Report and Written Opinion for PCT Application No. PCT/US2025/034283, dated Oct. 22, 2025, 29 pages.
Non-Final Office Action for U.S. Appl. No. 19/242,849, filed Jan. 12, 2026, 15 pages.
Notice of Allowance for U.S. Appl. No. 19/030,236, dated Mar. 31, 2026, 8 pages.
Notice of Allowance for U.S. Appl. No. 19/396,014, dated Apr. 21, 2026, 11 pages.
Non-Final Office Action for U.S. Appl. No. 19/242,810, dated Feb. 13, 2026, 10 pages.
Non-Final Office Action for U.S. Appl. No. 19/242,849, dated May 4, 2026, 11 pages.
Non-Final Office Action for U.S. Appl. No. 19/573,690, dated May 18, 2026, 13 pages.
Preliminary Office Action for Brazilian Application No. BR112023003735-2, dated Apr. 28, 2026, 7 pages.
Office Action for Chinese Application No. 202180053933.5, dated May 1, 2026, 6 pages.
Communication pursuant to Rule 114(2) EPC, for EP Application No. 21865183.4, dated May 12, 2026, 28 pages.
Kambali, I., "Calculated Radioactivity Yields of Cu-64 from Proton-Bombarded Ni-64 Targets Using SRIM Codes," Atom Indonesia, 2014, vol. 40, No. 3, pp. 129-134.
Le VAN So., et al., "Radiochemical separation and quality assessment for the 68Zn target based 64Cu radioisotope production," Journal of Radioanalytical and Nuclear Chemistry, Aug. 1, 2008, vol. 277, issue 2, (16) pp. 451-466.
Rayyes, A.H., et al., "Cyclotron Produced Radionuclides: Emerging Positron Emitters for Medical Applications: 64Cu and 1241," in IAEA Radioisotopes and Radiopharmaceuticals Reports No. 1, Mar. 2016, 80 pages.
Svedjehed; J., et al., "Automated, cassette-based isolation and formulation of high-purity [61 CU]CuCI2 from solid Ni targets," EJNMMI Radiopharmacy and Chemistry, 2020, vol. 5, No. 21, 14 pages.
Notice of Allowance for U.S. Appl. No. 19/242,849 dated May 28, 2026, 9 pages.
Examination Report No. 1 for Australian Application No. 2021335596, dated May 9, 2026, 5 pages.
Office Action for Canadian Patent Application No. 3192205, mailed Jun. 15, 2026, 4 Pages.
Non-Final Office Action for U.S. Appl. No. 19/676,489 dated Jul. 27, 2026, 13 pages.
Restriction Requirement for U.S. Appl. No. 18/745,888, dated Jun. 5, 2026, 11 pages.

* cited by examiner

PURIFICATION PROCESS FOR THE PREPARATION OF NON-CARRIER ADDED COPPER-64

CROSS-REFERENCE TO RELATED APPLICATIONS

This application is a continuation of U.S. application Ser. No. 18/745,896 filed Jun. 17, 2024, which claims priority to U.S. Provisional Application No. 63/654,662, filed May 31, 2024; additionally, U.S. application Ser. No. 18/745,896 filed Jun. 17, 2024, is also a continuation-in-part of U.S. application Ser. No. 18/238,951, filed Aug. 28, 2023, now U.S. Pat. No. 12,148,542 issued Nov. 19, 2024, which is a continuation of U.S. application Ser. No. 17/993,186, filed Nov. 23, 2022, now issued as U.S. Pat. No. 11,798,701 issued Oct. 24, 2023, which is a continuation of U.S. application Ser. No. 17/894,874, now issued as U.S. Pat. No. 11,581,103, filed Aug. 24, 2022, which is a continuation of U.S. application Ser. No. 17/446,443, now issued as U.S. Pat. No. 11,521,762, filed Sep. 3, 2021, which claims the priority of U.S. Provisional Application Ser. No. 63/074,356, filed Sep. 3, 2020, the disclosures of which are hereby incorporated by reference in their entirety.

FIELD

The present disclosure relates to compositions comprising high levels of high specific activity copper-64, and process for preparing said compositions.

BACKGROUND

Diagnostic nuclear medicine uses two imaging techniques—single photon emission tomography (SPECT) and positron emission tomography (PET), often in conjunction with computerized tomography (CT) or magnetic resonance imaging (MRI). Of the two imaging techniques, PET provides higher resolution images and quantitative information. The enhanced capabilities of PET have generated higher demand for radiopharmaceutical agents that are capable of being imaged using this technique, thus necessitating the production of commercial quantities of radioactive precursors capable of PET for routine clinical use.

Common clinically-used PET isotopes include oxygen-15 ($^{15}O$), nitrogen-13 ($^{13}N$), carbon-11 ($^{11}C$), fluorine-18 ($^{18}F$), and gallium-68 ($^{68}Ga$). Each of these isotopes, however, has a relatively short half-life, which necessitates producing them in close proximity to the PET imaging device and incorporating them into imaging agents before excessive radioactive decay or drug product decomposition occurs. A generator system for $^{68}Ga$ is available but it can be difficult to obtain and severely limits the number of doses that can be prepared in a day. To address the limitations of the short half-life radionuclides, PET isotopes with relatively longer half-lives have been investigated for development of new diagnostic PET agents.

Copper-64 ($^{64}Cu$) is a 'non-standard isotope' that can be used in diagnostic nuclear medicine. It is a radionuclide with excellent characteristics for PET imaging. Its average positron energy of 278.2 keV provides high resolution images, and its moderate half-life (12.7 h) is suitably long to allow for production, purification, incorporation into a carrier molecule (e.g., peptide, small-molecule, antibody, etc.) and distribution to medical facilities as an end-use product.

For widespread availability of $^{64}Cu$ on a commercial scale, large quantities of $^{64}Cu$ (i.e., Ci or GBq amounts) must be produced and isolated in a highly pure and chemically useful form (e.g., $^{64}Cu$ copper chloride) for use as a radioactive precursor. Preparations of $^{64}Cu$ copper chloride have been produced from isotopically enriched nickel-64 ($^{64}Ni$) targets, and the $^{64}Cu$ has been purified using ion exchange chromatography. In references located as of 2020, the highest reported amount of $^{64}Cu$ produced was 1.5 Ci, reported at end of bombardment (EOB). While this amount is sufficient for preparing patient doses, when factoring in decay and yield loss during manufacturing (i.e., formulation, sterilization, dispense, quality control, packaging and shipment)—1.5 Ci of $^{64}Cu$ at EOB may yield 50 patient doses in a best-case scenario (assuming an average patient dose of 4 mCi, 32 h for manufacturing and shipment and 15% yield loss). The number of theoretical patient doses may be significantly improved by increasing the available quantity of $^{64}Cu$ copper chloride precursor. The $^{64}Cu$ must be of high chemical and radionuclidic purity.

Specific activity (i.e., activity of $^{64}Cu$ per mass of total Cu) of $^{64}Cu$ copper chloride is an indicator of its chemical purity and is often expressed in units of mCi/μg or Ci/mmol. In references located as of 2020, the highest reported specific activity of purified $^{64}Cu$ copper chloride was 348 mCi/μg Cu. This is sufficient for radiolabeling, but improvements in specific activity may improve the purity and reactivity of a radioactive precursor, thereby decreasing the required amount of carrier molecule necessary in production of a radiolabeled pharmaceutical. This has implications for patient safety and may enhance the diagnostic capability of a radiopharmaceutical. Improvements in specific activity of $^{64}Cu$ may be made by increasing the produced quantity of radioactive precursor, limiting the potential for introduction of trace metallic contaminants and creating a robust purification process.

If $^{64}Cu$ were widely available, it would enhance the capabilities of existing PET centers and would also allow PET studies to be performed at medical centers that do not have an on-site $^{68}Ge/^{68}Ga$ generator and/or do not rely on a regional cyclotron. Described herein are methods of making purified $^{64}Cu$ having improved chemical and radionuclidic purities and a specific activity that is favorable for supplying commercial clinical needs of PET and medical centers.

SUMMARY

Among the various aspect of the present disclosure are compositions comprising high levels of $^{64}Cu$ with high purity and high specific activity and processes for preparing said compositions.

One aspect of the present disclosure provides a composition comprising from about 2 Ci to about 15 Ci of $^{64}Cu$ at end of bombardment (EOB). The composition is obtained from a single target during one cyclotron run. The composition may have a specific activity of at least about 25 mCi $^{64}Cu$/μg Cu, at least about 30 mCi $^{64}Cu$/μg Cu, at least about 35 mCi $^{64}Cu$/μg Cu, at least about 40 mCi $^{64}Cu$/μg Cu, at least about 45 mCi $^{64}Cu$/μg Cu, at least about 50 mCi $^{64}Cu$/μg Cu, at least about 55 mCi $^{64}Cu$/μg Cu, at least about 60 mCi $^{64}Cu$/μg Cu, at least about 65 mCi $^{64}Cu$/μg Cu, at least about 70 mCi $^{64}Cu$/μg Cu, at least about 75 mCi $^{64}Cu$/μg Cu, at least about 80 mCi $^{64}Cu$/μg Cu, at least about 85 mCi $^{64}Cu$/μg Cu, at least about 90 mCi $^{64}Cu$/μg Cu, at least about 95 mCi $^{64}Cu$/μg Cu, at least about 100 mCi $^{64}Cu$/μg Cu, at least about 105 mCi $^{64}Cu$/μg Cu, at least about 110 mCi $^{64}Cu$/μg Cu, at least about 115 mCi $^{64}Cu$/μg Cu, at least about 120 mCi $^{64}Cu$/μg Cu, at least about 125 mCi $^{64}Cu$/μg Cu, at least about 130 mCi $^{64}Cu$/μg Cu, at least about 135 mCi $^{64}Cu/\mu g$ Cu, at least about 140 mCi $^{64}Cu/\mu g$ Cu, at least about 145 mCi $^{64}Cu/\mu g$ Cu, or at least about 150 mCi $^{64}Cu/\mu g$ Cu. The composition may have a specific activity of up to about 3750 mCi $^{64}Cu/\mu g$ Cu, up to about 3775 mCi $^{64}Cu/\mu g$ Cu, up to about 3800 mCi $^{64}Cu/\mu g$ Cu, up to about 3825 mCi $^{64}Cu/\mu g$ Cu, or up to about 3850 mCi $^{64}Cu/\mu g$ Cu. The composition may have a specific activity at least about 30 mCi $^{64}Cu/\mu g$ Cu up to about 3750 mCi $^{64}Cu/\mu g$ Cu, at least about 30 mCi $^{64}Cu/\mu g$ Cu up to about 3775 mCi $^{64}Cu/\mu g$, at least about 30 mCi $^{64}Cu/\mu g$ Cu up to about 3800 mCi $^{64}Cu/\mu g$ Cu, at least about 30 mCi $^{64}Cu/\mu g$ Cu up to about 3825 mCi $^{64}Cu/\mu g$ Cu, or at least about 30 mCi $^{64}Cu/\mu g$ Cu up to about 3850 mCi $^{64}Cu/\mu g$ Cu. The composition may have a specific activity of at least about 40 mCi $^{64}Cu/\mu g$ Cu up to about 3750 mCi $^{64}Cu/\mu g$ Cu, at least about 40 mCi $^{64}Cu/\mu g$ Cu up to about 3775 mCi $^{64}Cu/\mu g$, at least about 40 mCi $^{64}Cu/\mu g$ Cu up to about 3800 mCi $^{64}Cu/\mu g$ Cu, at least about 40 mCi $^{64}Cu/\mu g$ Cu up to about 3825 mCi $^{64}Cu/\mu g$ Cu, or at least about 40 mCi $^{64}Cu/\mu g$ Cu up to about 3850 mCi $^{64}Cu/\mu g$ Cu. The composition may have a specific activity of at least about 50 mCi $^{64}Cu/\mu g$ Cu up to about 3750 mCi $^{64}Cu/\mu g$ Cu, at least about 50 mCi $^{64}Cu/\mu g$ Cu up to about 3775 mCi $^{64}Cu/\mu g$ Cu, at least about 50 mCi $^{64}Cu/\mu g$ Cu up to about 3800 mCi $^{64}Cu/\mu g$ Cu, at least about 50 mCi $^{64}Cu/\mu g$ Cu up to about 3825 mCi $^{64}Cu/\mu g$ Cu, or at least about 50 mCi $^{64}Cu/\mu g$ Cu up to about 3850 mCi $^{64}Cu/\mu g$ Cu. The composition may have a specific activity at least about 75 mCi $^{64}Cu/\mu g$ Cu up to about 3750 mCi $^{64}Cu/\mu g$ Cu, about 3775 mCi $^{64}Cu/\mu g$ Cu about 3800 mCi $^{64}Cu/\mu g$ Cu, about 3825 mCi $^{64}Cu/\mu g$ Cu, or about 3850 mCi $^{64}Cu/\mu g$ Cu. The composition may have a specific activity at least about 100 mCi $^{64}Cu/\mu g$ Cu up to about 3750 mCi $^{64}Cu/\mu g$ Cu, about 3775 mCi $^{64}Cu/\mu g$ Cu about 3800 mCi $^{64}Cu/\mu g$ Cu. In certain aspects, the composition has a specific activity up to about 3800 mCi $^{64}Cu/\mu g$ Cu. In some embodiments, the composition comprises a solution of hydrochloric acid, such that the $^{64}Cu$ exists as $^{64}CuCl_2$.

A further aspect of the present disclosure encompasses a process for preparing the $^{64}Cu$ from $^{64}Ni$. The process comprises (a) bombarding a cyclotron target comprising $^{64}Ni$ with a proton beam to generate a bombarded target; (b) stripping the bombarded target with a volume of HCl having a molarity of about 6 M to about 12.1 M to form a strip solution comprising $^{64}Ni$ and $^{64}Cu$; and (c) purifying the $^{64}Cu$ from the strip solution by ion exchange chromatography, wherein the ion exchange chromatography comprises (i) passing the strip solution through a column comprising an ion exchange resin such that $^{64}Cu$ binds to the ion exchange resin and $^{64}Ni$ passes through the column as a flow-through; (ii) rinsing the column with a volume of HCl having a molarity of about 3 M to about 6 M; and (iii) adding a volume of HCl having a molarity of about 0.5 M to about 3 M to the column to elute the $^{64}Cu$ from the ion exchange resin and collecting an eluate comprising $^{64}Cu$.

Another aspect of the present disclosure encompasses an additional process for preparing $^{64}Cu$ from $^{64}Ni$, wherein the $^{64}Cu$ is purified by a combination of extraction chromatography and ion exchange chromatography. The process comprises (a) bombarding a cyclotron target comprising $^{64}Ni$ with a proton beam to generate a bombarded target; (b) stripping the bombarded target with a volume of HCl having a molarity of about 6 M to about 12.1 M to form a strip solution comprising $^{64}Ni$, $^{64}Cu$, $^{61}Co$, and other or more other metals; and (c) purifying the $^{64}Cu$ from the strip solution by chromatography, wherein the chromatography comprises (i) passing the strip solution through a first column comprising an extraction resin connected in series to a second column comprising an ion exchange resin, such that the one or more other metals binds to the extraction resin in the first column, $^{64}Cu$ and $^{61}Co$ bind to the ion exchange resin in the second column, and $^{64}Ni$ passes through both columns as a first flow-through fraction. The process further comprises (ii) rinsing the first and second columns with a volume of HCl having a molarity of about 6 M to about 12.1 M to remover residual $^{64}Ni$ as a second flow-through fraction; (iii) rinsing the second column with a volume of HCl having a molarity of about 3 M to about 6 M to elute $^{61}Co$ as a first waste fraction; (iv) rinsing the second column with a volume of NaCl having a molarity of about 3 M to 6 M in HCl having a molarity of about 0.01 M to about 3 M or with a volume of HCl having a molarity of about 3 M to about 6 M to elute residual $^{61}Co$ as a second waste fraction; and (v) adding a volume of HCl having a molarity of about 0.01 M to about 3 M to the second column to elute the $^{64}Cu$ as a product fraction comprising $^{64}Cu$.

Another aspect of the composition encompasses a composition for use as a radioactive precursor comprising from 2 Ci to 15 Ci of copper-64 ($^{64}Cu$), and having a specific activity from about 50 mCi $^{64}Cu/\mu g$ Cu up to about 3800 mCi $^{64}Cu/\mu g$ Cu, wherein the composition comprises chemical and radionuclidic purities suitable for positron emission tomography (PET).

Other aspects and iterations of the present disclosure are detailed below.

DETAILED DESCRIPTION

Figure 1:
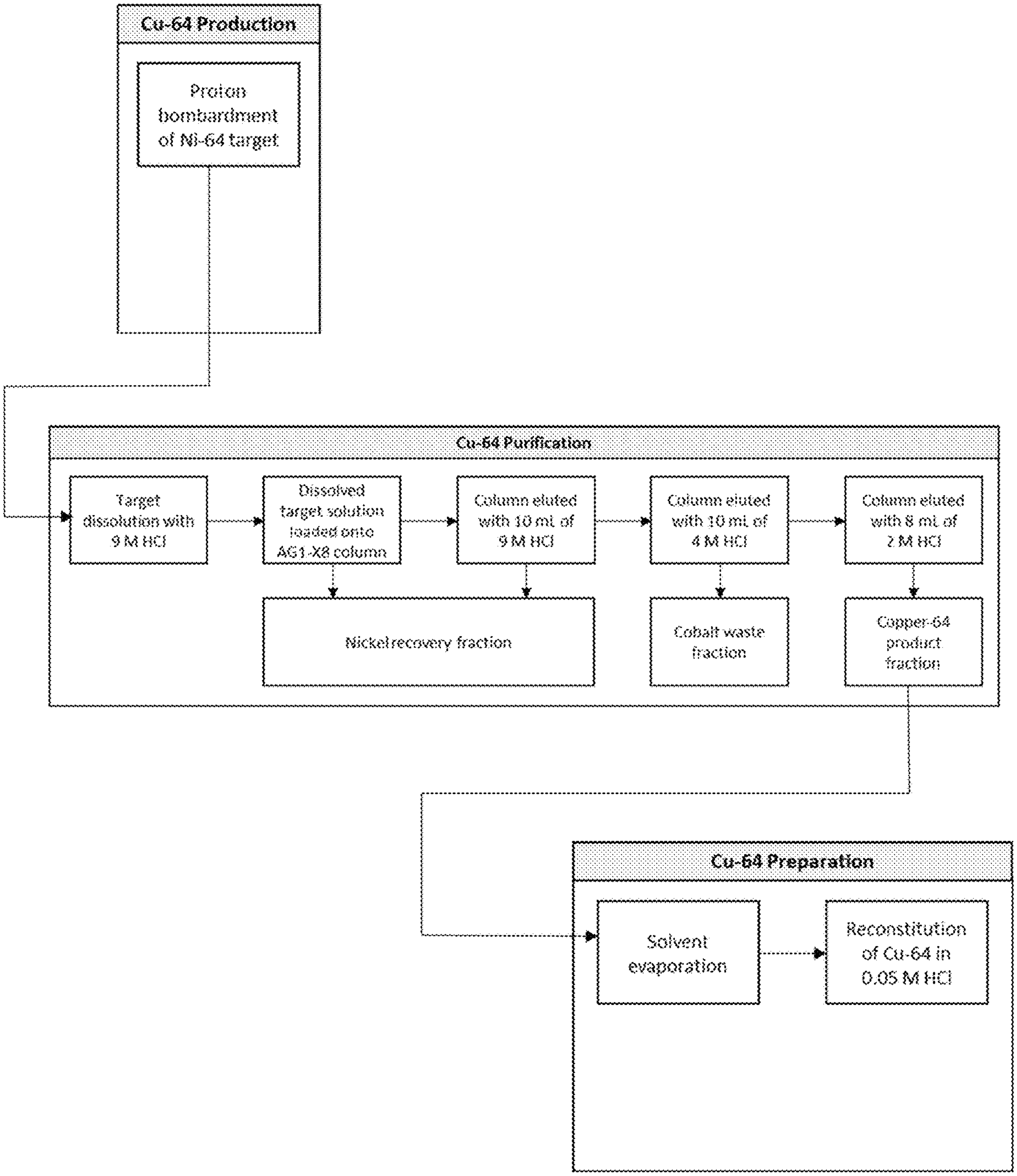
FIG. 1 presents a schematic of the purification process comprising ion exchange chromatography.

Provided herein are compositions comprising high levels of high specific activity $^{64}Cu$ and processes for preparing said compositions. The $^{64}Cu$ compositions described herein are suitable for administration to a human patient in need thereof. The $^{64}Cu$ compositions described herein are suitable for administration via injection. The processes disclosed herein are able to produce high levels of $^{64}Cu$ from a single target during one continuous cyclotron bombardment (i.e., cyclotron run). The $^{64}Cu$ produced by these processes has a high specific activity, as well as high chemical and radionuclidic purities. Favorably, the $^{64}Cu$ compositions produced by the processes disclosed herein also have low levels of metal impurities such as cobalt, iron, nickel and lead. The $^{64}Cu$ compositions produced by the processes disclosed herein also have low levels of copper-67 ($^{67}Cu$) or an absence of $^{67}Cu$ (i.e., zero ppm $^{67}Cu$). The $^{64}Cu$ compositions produced by the processes disclosed herein also have low levels of zinc-68 ($^{68}Zn$) or an absence of $^{68}Zn$ (i.e., zero ppm $^{68}Zn$). The $^{64}Cu$ compositions produced by the processes disclosed herein also have low levels of or an absence of any element or isotope with a mass number of 67 or greater. The $^{64}Cu$ compositions produced by the processes disclosed herein also have low levels of or an absence of any element or isotope with a mass number of 68 or greater. The $^{64}Cu$ compositions produced by the processes disclosed herein have an absence of zinc-based target source materials.

(I) Compositions

The $^{64}$Cu compositions disclosed herein comprise high levels of high specific activity $^{64}$Cu. The $^{64}$Cu compositions described herein include isolated $^{64}$Cu compositions, wherein the $^{64}$Cu has been removed or stripped from the target. In general, the $^{64}$Cu compositions comprise up to about 15 Ci of $^{64}$Cu and have specific activities up to about 3800 mCi $^{64}$Cu/μg Cu. The isolated $^{64}$Cu compositions comprise from about 2 Ci to about 15 Ci of $^{64}$Cu and have specific activities from 30 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 40 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 45 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 50 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 60 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 70 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 80 mCi $^{64}$Cu/μg Cu up to about 3800 mCi $^{64}$Cu/μg Cu. The isolated $^{64}$Cu compositions comprise from about 2 Ci to about 15 Ci of $^{64}$Cu and have specific activities from 90 mCi $^{64}$Cu/μg Cu up to about 3800 mCi $^{64}$Cu/μg Cu. In some The $^{64}$Cu compositions may be prepared by the processes described below in sections (II) and (III).

The $^{64}$Cu activity (Ci or Bq) may be measured by gamma spectroscopy (e.g., high purity germanium (HPGe) detector), a dose calibrator, or similar means. Specific activity (mCi $^{64}$Cu/μg Cu) may be determined by measuring the mass of Cu by a variety of methods including inductively coupled plasma optical emission spectroscopy (ICP-OES), inductively coupled plasma mass spectrometry (ICP-MS), or titration. The compositions described herein may be suitable for administration to a human patient in need thereof. The compositions described herein may be suitable for administration via a single dose vial. In one aspect, the compositions described herein comprise about 35 MBq to about 40 MBq of $^{64}$Cu per 1 mL of the composition in a single dose vial. In one aspect, the compositions described herein comprise about 35 MBq to about 40 MBq of $^{64}$Cu DOTATATE per 1 mL of the composition in a single dose vial. In another aspect, the compositions described herein comprise about 36 MBq to about 38 MBq of $^{64}$Cu per 1 mL of the composition in a single dose vial. In another aspect, the compositions described herein comprise about 36 MBq to about 38 MBq of $^{64}$Cu DOTATATE per 1 mL of the composition in a single dose vial. In another aspect, the compositions described herein comprise about 36.5 MBq to about 37.5 MBq of $^{64}$Cu per 1 mL of the composition in a single dose vial. In another aspect, the compositions described herein comprise about 36.5 MBq to about 37.5 MBq of $^{64}$Cu DOTATATE per 1 mL of the composition in a single dose vial. In another aspect, the compositions described herein comprise about 37.0 MBq of $^{64}$Cu per 1 mL of the composition in a single dose vial. In another aspect, the compositions described herein comprise about 37.0 MBq of $^{64}$Cu DOTATATE per 1 mL of the composition in a single dose vial. In another aspect, the compositions described herein comprise about 145 to about 150 MBq of $^{64}$Cu DOTATATE in a single dose vial. In another aspect, the compositions described herein comprise about 145 to about 150 MBq per of $^{64}$Cu in a single dose vial. In another aspect, the compositions described herein comprise about 145 to about 150 MBq of $^{64}$Cu in a single dose vial, wherein the $^{64}$Cu composition further comprises DOTA and/or DOTAGA.

The composition in the single dose vial suitable for administration to a human patient in need thereof may be isolated or aliquoted from a composition comprising from 2 Ci to 15 Ci of $^{64}$Cu and having a specific activity from 50 mCi to 3850 mCi $^{64}$Cu/μg Cu. The composition in the single dose vial suitable for administration to a human patient in need thereof may be isolated or aliquoted from a composition comprising from 3 Ci to 15 Ci of $^{64}$Cu and having a specific activity from 50 mCi to 3850 mCi $^{64}$Cu/μg Cu. The composition in the single dose vial suitable for administration to a human patient in need thereof may be isolated or aliquoted from a composition comprising from 4 Ci to 15 Ci of $^{64}$Cu and having a specific activity from 50 mCi to 3850 mCi $^{64}$Cu/μg Cu. The composition in the single dose vial suitable for administration to a human patient in need thereof may be isolated or aliquoted from a composition comprising from 5 Ci to 15 Ci of $^{64}$Cu and having a specific activity from 50 mCi to 3850 mCi $^{64}$Cu/μg Cu.

The composition in the single dose vial suitable for administration to a human patient in need thereof may be isolated or aliquoted from a composition comprising from 2 Ci to 15 Ci of $^{64}$Cu and having a specific activity from 100 mCi to 3850 mCi $^{64}$Cu/μg Cu. The composition in the single dose vial suitable for administration to a human patient in need thereof may be isolated or aliquoted from a composition comprising from 3 Ci to 15 Ci of $^{64}$Cu and having a specific activity from 100 mCi to 3850 mCi $^{64}$Cu/μg Cu. The composition in the single dose vial suitable for administration to a human patient in need thereof may be isolated or aliquoted from a composition comprising from 4 Ci to 15 Ci of $^{64}$Cu and having a specific activity from 100 mCi to 3850 mCi $^{64}$Cu/μg Cu. The composition in the single dose vial suitable for administration to a human patient in need thereof may be isolated or aliquoted from a composition comprising from 5 Ci to 15 Ci of $^{64}$Cu and having a specific activity from 100 mCi to 3850 mCi $^{64}$Cu/μg Cu.

In general, the compositions disclosed herein comprise from about 2 Ci to about 15 Ci of $^{64}$Cu at the end of bombardment (EOB). The level of $^{64}$Cu may be determined at EOB or a later time point. Persons skilled in the art understand that the level of $^{64}$Cu activity decreases over time. In some embodiments, the compositions may comprise from about 2 Ci to about 3 Ci, from about 3 Ci to about 4 Ci, from about 4 Ci to about 5 Ci, from about 5 Ci to about 6 Ci, from about 6 Ci to about 7 Ci, from about 7 Ci to about 8 Ci, from about 8 Ci to about 9 Ci, from about 9 Ci to about 10 Ci, from about 10 Ci to about 11 Ci, from about 11 Ci to about 12 Ci, from about 12 to about 13 Ci, from about 13 to about 14, or from about 14 to about 15 Ci of $^{64}$Cu. In other embodiments, the composition may comprise from about 4.0-4.5 Ci, from about 4.5-5.0 Ci, from about 5.0-5.5 Ci, from about 5.5-6.0 Ci, from about 6.0-6.5 Ci, from about 6.5-7.0 Ci, from about 7.0-7.5 Ci, from about 7.5-8.0 Ci, from about 8.0-8.5 Ci, from about 8.5-9.0 Ci, from about 9.0-12.0, from about 12.0-15.0, from about 4.0-5.5 Ci, from about 5.5-7.0 Ci, from about 6.0-7.5 Ci, from about 7.0-8.5 Ci, r from about 7.5-9.0 Ci, or from about 9.0-15.0 Ci of $^{64}$Cu.

In other embodiments, the compositions may comprise from about 2 Ci to about 5 Ci of $^{64}$Cu at EOB, from about 5 Ci to about 9 Ci of $^{64}$Cu at EOB, or from about 9 Ci to about 15 Ci at EOB. In other embodiments, the compositions may comprise from about 2 Ci to about 15 Ci of $^{64}$Cu at EOB. In further embodiments, the compositions may comprise from about 2 Ci to about 5 Ci of $^{64}$Cu (at EOB) after about 2-4 h of bombardment, or about 5 Ci to about 9 Ci of $^{64}$Cu (at EOB) after about 6 h of bombardment, or about 4 Ci to about 15 Ci of $^{64}$Cu (at EOB) after about 8-12 h of bombardment.

Each of the compositions disclosed herein may be produced during a single cyclotron run and/or may be obtained from a single cyclotron bombardment.

As a non-limiting example of a $^{64}$Cu composition production schedule, production of a $^{64}$Cu composition begins with the cyclotron bombardment of a target beginning on Day 0 until EOB. The EOB time may range from the afternoon to the evening of Day 0 or even earlier or longer in some instances. At EOB, the $^{64}$Cu is stripped or removed from the target and processed to form a $^{64}$Cu composition that has a high level of radionuclidic purity. The radionuclidic purity of the $^{64}$Cu composition is typically measured on Day 1, which is referred to as the Raw Material Calibration Time. In some cases, the raw material calibration time may occur about 6:00 am on Day 1. The $^{64}$Cu composition that is produced using the $^{64}$Cu composition is then sent to a location where it is administered to a patient on Day 2.

The radionuclidic purity of the $^{64}$Cu compositions disclosed herein is generally greater than about 95.0%, greater than about 96%, greater than about 97.0%, greater than about 98.0%, greater than about 98.5%, greater than about 99%, greater than about 99.5%, or greater than about 99.9% at the Raw Material Calibration Time.

As time passes, short-lived radioisotopes present in the $^{64}$Cu compositions will decay away which causes the radionuclidic purity of the $^{64}$Cu compositions to increase. Thus, another calculation of the radionuclidic purity is determined for $^{64}$Cu composition at the Drug Product Calibration Time, which is a set time on Day 2 that occurs shortly before the expiration of the $^{64}$Cu radiopharmaceutical. In some instances, the Drug Product Calibration Time is calculated for the radionulidic purity of the $^{64}$Cu composition that exists at 5:00 pm on Day 2, the day when the $^{64}$Cu radiopharmaceutical is administered to the patient.

The radionuclidic purity of the $^{64}$Cu compositions disclosed herein is generally greater than about greater than about 99%, greater than about 99.5%, greater than about 99.7%, greater than about 99.8%, or greater than about 99.9% at the Drug Product Calibration Time.

The specific activity of the $^{64}$Cu in the compositions disclosed herein may be greater than 25 mCi $^{64}$Cu/µg Cu, greater than 30 mCi $^{64}$Cu/µg Cu, greater than 35 mCi $^{64}$Cu/µg Cu, greater than 40 mCi $^{64}$Cu/µg Cu, greater than 45 mCi $^{64}$Cu/µg Cu, greater than 50 mCi $^{64}$Cu/µg Cu, greater than 75 mCi $^{64}$Cu/µg Cu, or greater than 100 mCi $^{64}$Cu/µg Cu at EOB. The specific activity of the $^{64}$Cu in the compositions disclosed herein may be as high as about 3800 mCi $^{64}$Cu/µg Cu at EOB. In other embodiments, the specific activity may range from about 50 mCi $^{64}$Cu/µg Cu to about 3800 mCi $^{64}$Cu/µg Cu, from about 75 mCi $^{64}$Cu/µg Cu to about 3800 mCi $^{64}$Cu/µg Cu, or from about 100 mCi $^{64}$Cu/µg Cu to about 3800 mCi $^{64}$Cu/µg Cu. Those skilled in the art understand that the specific activities of the compositions decrease over time. In various embodiments, the specific activity may range from about 100 mCi $^{64}$Cu/µg Cu to about 500 mCi $^{64}$Cu/µg Cu, from about 500 mCi $^{64}$Cu/µg Cu to about 1000 mCi $^{64}$Cu/µg Cu, from about 1000 mCi $^{64}$Cu/µg Cu to about 1500 mCi $^{64}$Cu/µg Cu, from about 1500 mCi $^{64}$Cu/µg Cu to about 2500 mCi $^{64}$Cu/µg Cu, from about 2500 mCi $^{64}$Cu/µg Cu to about 3000 mCi $^{64}$Cu/µg Cu, or from about 3000 mCi $^{64}$Cu/µg Cu to about 3800 mCi $^{64}$Cu/µg Cu. In some embodiments, the specific activity may range from about 350 $^{64}$Cu/µg Cu to about 2300 mCi $^{64}$Cu/µg Cu. In further embodiments, the specific activity may range from about 350 $^{64}$Cu/µg Cu to about 500 mCi $^{64}$Cu/µg Cu at EOB, from about 500 $^{64}$Cu/µg Cu to about 1000 mCi $^{64}$Cu/µg Cu at EOB, or from about 1000 $^{64}$Cu/µg Cu to about 2300 mCi $^{64}$Cu/µg Cu at EOB.

In general, the $^{64}$Cu compositions disclosed herein comprise low levels of metal contaminants. The metal contaminants may be radioactive or nonradioactive. The metal contaminants may include calcium, cobalt, copper, gold, iron, lead, mercury, nickel, and zinc. For example, the 2 M HCl eluate described below in Example 5 comprises 0 ppm Au, 0 ppm Hg, <0.02 ppm Co, <0.2 ppm Fe, <0.4 ppm Pb, <0.5 ppm Ni, <0.6 ppm Cu, and <1.5 ppm Zn. In general, the $^{64}$Cu compositions disclosed herein comprise less than about less than about 6 ppm total, less than about 5 ppm total, less than about 4 ppm total, or less than about 3 ppm total of cobalt, copper, gold, iron, lead, mercury, nickel, and zinc. In general, the $^{64}$Cu compositions disclosed herein comprise less than about less than about 6 ppm total, less than about 5 ppm total, less than about 4 ppm total, or less than about 3 ppm total of cobalt, $^{67}$Cu, gold, iron, lead, mercury, nickel, and/or zinc. In general, the $^{64}$Cu compositions disclosed herein comprise less than about less than about 6 ppm total, less than about 5 ppm total, less than about 4 ppm total, or less than about 3 ppm total of $^{68}$Zn. The $^{64}$Cu compositions disclosed herein may comprise less than about less than about 6 ppm total, less than about 5 ppm total, less than about 4 ppm total, less than about 3 ppm total, less than about 2 ppm total, less than about 1 ppm total, or less than about 0.5 ppm total of any element or isotope with a mass number of 67 or greater. The $^{64}$Cu compositions disclosed herein may comprise less than about less than about 6 ppm total, less than about 5 ppm total, less than about 4 ppm total, less than about 3 ppm total, less than about 2 ppm total, less than about 1 ppm total, or less than about 0.5 ppm total of any element or isotope with a mass number of 68 or greater.

The composition comprising $^{64}$Cu may have a total content of less than about 25 ppm, less than about 10 ppm, less than about 5 ppm, less than about 1 ppm, less than about 0.5 ppm, and/or less than about 0.1 ppm of $^{67}$Cu (e.g., 0 ppm of $^{67}$Cu). The composition comprising $^{64}$Cu may have a total content of less than about 50 ppb, less than about 25 ppb, less than about 10 ppb, less than about 5 ppb, less than about 1 ppb, less than about 0.5 ppb, and/or less than about 0.1 ppb of $^{67}$Cu (e.g., 0 ppb of $^{67}$Cu). The composition comprising $^{64}$Cu may have a total content of less than about 25 ppm, less than about 10 ppm, less than about 5 ppm, less than about 1 ppm, less than about 0.5 ppm, and/or less than about 0.1 ppm of $^{68}$Zn (e.g., 0 ppm of $^{68}$Zn). The composition comprising $^{64}$Cu may have a total content of less than about 50 ppb, less than about 25 ppb, less than about 10 ppb, less than about 5 ppb, less than about 1 ppb, less than about 0.5 ppb, and/or less than about 0.1 ppb of $^{68}$Zn (e.g., 0 ppb of $^{68}$Zn). The composition comprising $^{64}$Cu may have a total content of less than about 25 ppm, less than about 10 ppm, less than about 5 ppm, less than about 1 ppm, less than about 0.5 ppm, and/or less than about 0.1 ppm of any element or isotope with a mass number of 67 or greater. The composition comprising $^{64}$Cu may have a total content of less than about 50 ppb, less than about 25 ppb, less than about 10 ppb, less than about 5 ppb, less than about 1 ppb, less than about 0.5 ppb, and/or less than about 0.1 ppb of any element or isotope with a mass number of 67 or greater. The composition comprising $^{64}$Cu may have a total content of less than about 25 ppm, less than about 10 ppm, less than about 5 ppm, less than about 1 ppm, less than about 0.5 ppm, and/or less than about 0.1 ppm of any element or isotope with a mass number of 68 or greater. The composition comprising $^{64}$Cu may have a total content of less than about 50 ppb, less than about 25 ppb, less than about 10 ppb, less than about 5 ppb, less than about 1 ppb, less than about 0.5 ppb, and/or less than about 0.1 ppb of any element or isotope with a mass number of 68 or greater.

The composition may also comprise from 0 to about 1.0%, from 0 to about 0.7%, from 0 to about 0.5%, from 0 to about 0.3%, and/or from 0 to about 0.1% of $^{67}$Cu by weight of the composition. The composition may also comprise from 0 to about 0.01%, from 0 to about 0.005%, from 0 to about 0.001%, or from 0 to about 0.0005% of $^{67}$Cu by weight of the composition. The composition may also comprise from 0 to about 1.0%, from 0 to about 0.7%, from 0 to about 0.5%, from 0 to about 0.3%, and/or from 0 to about 0.1% of $^{67}$Cu by weight of the composition. The composition may also comprise from 0 to about 0.01%, from 0 to about 0.005%, from 0 to about 0.001%, or from 0 to about 0.0005% of $^{68}$Zn by weight of the composition. The composition may also comprise from 0 to about 1.0%, from 0 to about 0.7%, from 0 to about 0.5%, from 0 to about 0.3%, and/or from 0 to about 0.1% of $^{67}$Cu by weight of the composition. The composition may also comprise from 0 to about 0.01%, from 0 to about 0.005%, from 0 to about 0.001%, or from 0 to about 0.0005% of any element or isotope with a mass number of 67 or greater by weight of the composition. The composition may also comprise from 0 to about 0.01%, from 0 to about 0.005%, from 0 to about 0.001%, or from 0 to about 0.0005% of any element or isotope with a mass number of 68 or greater by weight of the composition.

The composition comprising $^{64}$Cu may have a total content of less than or equal to about 10 μg/mL, less than or equal to about 9 μg/mL, less than or equal to about 8 μg/mL, less than or equal to about 7 μg/mL, less than or equal to about 6 μg/mL, less than or equal to about 5 μg/mL, less than or equal to about 4 μg/mL, less than or equal to about 3 μg/mL, less than or equal to about 2 μg/mL, less than or equal to about 1 μg/mL, or about 0 μg/mL of $^{67}$Cu. The composition comprising $^{64}$Cu may have a total content of less than or equal to about 10 μg/mL, less than or equal to about 9 μg/mL, less than or equal to about 8 μg/mL, less than or equal to about 7 μg/mL, less than or equal to about 6 μg/mL, less than or equal to about 5 μg/mL, less than or equal to about 4 μg/mL, less than or equal to about 3 μg/mL, less than or equal to about 2 μg/mL, less than or equal to about 1 μg/mL, or about 0 μg/mL of $^{68}$Zn. The composition comprising $^{64}$Cu may have a total content of less than or equal to about 10 μg/mL, less than or equal to about 9 μg/mL, less than or equal to about 8 μg/mL, less than or equal to about 7 μg/mL, less than or equal to about 6 μg/mL, less than or equal to about 5 μg/mL, less than or equal to about 4 μg/mL, less than or equal to about 3 μg/mL, less than or equal to about 2 μg/mL, less than or equal to about 1 μg/mL, or about 0 μg/mL of any element or isotope with a mass number of 67 or greater. The composition comprising $^{64}$Cu may have a total content of less than or equal to about 10 μg/mL, less than or equal to about 9 μg/mL, less than or equal to about 8 μg/mL, less than or equal to about 7 μg/mL, less than or equal to about 6 μg/mL, less than or equal to about 5 μg/mL, less than or equal to about 4 μg/mL, less than or equal to about 3 μg/mL, less than or equal to about 2 μg/mL, less than or equal to about 1 μg/mL, or about 0 μg/mL of any element or isotope with a mass number of 68 or greater.

The $^{64}$Cu compositions disclosed herein may comprise a solution of hydrochloric acid (HCl) such that the solution comprises $^{64}CuCl_2$. The solution of HCl may comprise from about 0.005 M to about 3.0 M of HCl. In some embodiments, the solution of HCl may comprise HCl at a molarity from about 0.01 M to about 2.0 M, from about 0.02 M to about 1.0 M, or from 0.04 M to about 0.06 M. In specific embodiments, the $^{64}$Cu compositions may comprise a solution of about 0.05 M HCl.

In some embodiments, the compositions disclosed herein may further comprise at least one bifunctional chelating agent such that the copper may complex with the bifunctional chelating agent. The bifunctional chelating agent may be a macrocyclic compound, a bridged macrocyclic compound, a bicyclic compound, or an acyclic compound. Examples of suitable bifunctional chelating agents include 1,4,7,10-tetraazacyclododecane-N,N',N",N"-tetraacetic acid (DOTA), DOTAGA, 1,4,7-triazacyclononane-1,4,7-triacetic acid (NOTA), 1,4,8,11-tetraazacyclotetradecane-N,N',N", N"-tetraacetic acid (TETA), 5-(8-methyl-3,6,10,13,16,19-hexaaza-bicyclo[6.6.6]icosan-1-ylamino)-5-oxopentanoic acid (MeCOSar), 5-((8-amino-3,6,10,13,16,19-hexaazabicyclo(6.6.6)eicos-1-yl)amino)-5-oxopentanoic acid (sar-CO2H), di- and trimethylthiazolyl 1,4,7-triazacyclononane (TACN), diethylenetriaminepentaacetic acid (DTPA), 3,6,9,15-tetraazabicyclo[9.3.1]pentadeca-1(15), 11,13-triene-3,6,9-triacetic acid (PCTA), analogs, or derivatives thereof. In specific embodiments, the bifunctional chelating agent may be DOTA or DOTAGA. The bifunctional chelating agent may be linked to a cell targeting agent such as a peptide, protein, antibody, or fragment thereof.

(II) Processes for Producing Copper-64—Purification by Ion Exchange Chromatography Also provided herein are processes for preparing $^{64}$Cu from $^{64}$Ni, wherein the $^{64}$Cu has high specific activity, high chemical purity, and high radionuclidic purity. $^{64}$Cu is formed when a $^{64}$Ni nucleus captures a proton and then emits a neutron as shown in the following reaction, $^{64}Ni+p\rightarrow^{64}Cu+n$. Proton-induced production of $^{64}$Cu occurs in a cyclotron. The processes disclosed herein are "non-carrier added" in that no inactive material or carrier is intentionally added during the production process.

The processes disclosed herein are able to produce $^{64}$Cu in high yield and with high specific activity in one cyclotron run. Stated another way, high yield and high specific activity compositions comprising $^{64}$Cu are obtainable from a single cyclotron target during one cyclotron run. Depending upon the various parameters, yields as high as about 40 Ci of $^{64}$Cu may be achieved using the processes disclosed herein.

The production process comprises bombarding a $^{64}$Ni target with a proton beam such that $^{64}$Cu is produced, and cobalt-61 ($^{61}$Co) is produced as a by-product. The next step of the process comprises stripping the metals from the bombarded target with a strong acid (e.g., 6 M to about 12.1 M HCl) to form a strip solution. The last step of the production process comprises purifying the $^{64}$Cu by ion exchange chromatography. The ion exchange chromatography process comprises (i) passing the strip solution through a column comprising an ion exchange resin such that $^{64}$Cu binds to the ion exchange resin and $^{64}$Ni passes through the column as a flow-through, (ii) rinsing the column with a volume of HCl having a molarity of about 3 M to about 6 M and (iii) adding a volume of HCl having a molarity of about 0.5 M to about 3 M to the column to elute the $^{64}$Cu from the ion exchange resin and collecting an eluate comprising $^{64}$Cu. FIG. 1 presents a schematic of an iteration of the process.

(a) Bombarding the Target

The proton-induced production of $^{64}$Cu via a $^{64}$Ni target occurs in a cyclotron. Suitable cyclotrons include low-energy cyclotrons (e.g., 3-20 MeV energy range) and medium-energy cyclotrons (e.g., 15-30 MeV range). The targets of said cyclotrons may be curved or flat. As detailed in Example 3 below, the present disclosure reveals that cyclotron targets may be bombarded at high currents with approximately 12 MeV to 13 MeV protons.

The cyclotron target may comprise a copper base layer that has been electroplated with gold to a thickness of about 50 μm. The gold-plated cyclotron target then may be plated with enriched $^{64}$Ni. The $^{64}$Ni may be enriched to about 98%, about 99%, about 99.6%, or about 99.9% $^{64}$Ni. The targeting mass of enriched $^{64}$Ni may range from about 40 mg to about 60 mg, from about 45 mg to about 55 mg, from about 48 mg to about 52 mg, or about 50 mg. The plating area may range from about 3.0 cm$^2$ to about 5.0 cm$^2$, from about 3.2 cm$^2$ to about 4.8 cm$^2$, from about 3.6 cm$^2$ to about 4.4 cm$^2$, from about 3.8 cm$^2$ to about 4.2 cm$^2$, or 4.0 cm$^2$. The plated layer of $^{64}$Ni may have a thickness from about 8 μm to about 20 μm, from about 10 μm to about 18 μm, from about 12 μm to about 16 μm, or about 14 μm.

In the processes disclosed herein, the $^{64}$Ni target area is bombarded with low energy protons to produce $^{64}$Cu. In general, the proton beam of the cyclotron is adjusted to have an energy of less than about 20 MeV on the target. In some embodiments, the energy of the proton beam at the target can range from about 5 MeV to about 20 MeV, from about 7 MeV to about 17 MeV, from about 10 MeV to about 15 MeV, from about 11 MeV to about 14 MeV, from about 10 MeV to about 14 MeV, from about 11 MeV to about 12 MeV, or from about 12 MeV to about 13 MeV. In specific embodiments, the actual beam energy at the target is about 12 MeV.

The current of the proton beam may range up to about 250 μA. In some embodiments, the current of the proton beam may range from about 10 μA to about 30 μA, about 30 μA to about 100 μA, from about 100 μA to about 175 μA, or from about 175 μA to about 250 μA. In specific embodiments, the current of the proton beam may range from about 190 μA to about 230 μA, or from about 200 μA to about 225 μA.

The proton beam hits the target area at an angle. In some embodiments, the angle of the proton beam may range from about 1° to about 20°, from about 2° to about 10°, from 2° to about 8°, from about 3° to about 6°, or about 4°. In other embodiments, the angle of the proton beam may be tangential to the target area.

In some embodiments, the target radius of the proton beam may range from about 24 cm to about 32 cm, from about 26 cm to about 30 cm, from about 27 cm to about 29 cm, or about 28 cm. In certain embodiments, the target radius of the proton beam may be about 27.9 cm. In some embodiments, the proton beam may strike about 20-25%, about 15-30%, or about 10-35% of the entire target face. In other embodiments, the total area covered by the beam may range from about 1 cm$^2$ to about 16 cm$^2$, from about 2 cm$^2$ to about 8 cm$^2$, from about 3 cm$^2$ to about 6 cm$^2$, or from about 3.5 cm$^2$ to about 4.5 cm$^2$. In still other embodiments, the total area covered by the beam may be about 3.0 cm$^2$, about 3.5 cm$^2$, about 4.0 cm$^2$, about 4.5 cm$^2$, about 5.0 cm$^2$, or about 6.0 cm$^2$.

The time of bombardment may range from about 0.5 h to about 24 h. In some embodiments, the time of bombardment may range from 0.5 h to about 8 h, from about 8 h to about 16 h, or from about 16 h to about 24 h. In other embodiments, the bombardments time may range from 1 h to about 8 h, from about 2 h to about 8 h, from about 4 h to about 8 h, from about 5 h to about 8 h, or about from 5 h to about 7 h. In certain embodiments, the bombardment time may range from about 1 h to about 6 h, from about 2 h to about 6 h, from about 3 h to about 6 h, from about 4 h to about 6 h, or from about be about 5 h to about 6 h. In other embodiments, the time of bombardment may be less than 8 h, less than 7.5 h, less than 7 h, less than 6.5 h, less than 6 h, less than 5.5 h, less than 5.0 h, less than 4.5 h, or less than 4 h. In further embodiments, the time of bombardment may be about 1 h, about 2 h, about 3 h, about 4 h, about 5 h, about 6 h, about 7 h, or about 8 h. In specific embodiments, the time of bombardment may range from about 2 h to about 4 h or the time of bombardment may be about 6 h.

In specific embodiments, a cyclotron target comprising 50 mg $^{64}$Ni is bombarded with a proton beam having an energy of about 12 MeV and a beam current of 200 μA or 225 μA for about 1 h, 2 h, 3 h, 4 h, or 6 h.

The bombarded target may comprise from about 2 Ci to about 15 Ci of $^{64}$Cu at the end of bombardment (EOB). The bombarded target also comprises unreacted $^{64}$Ni and $^{61}$Co that is also produced during the bombardment process. In various embodiments, the bombarded target may comprise from about 2 Ci to about 3Ci, from about 3 Ci to about 4 Ci, from about 4 Ci to about 5 Ci, from about 5 Ci to about 6 Ci, from about 6 Ci to about 7 Ci, from about 7 Ci to about 8 Ci, from about 8 Ci to about 9 Ci of $^{64}$Cu, from about 9 Ci to about 10 Ci, from about 10 Ci to about 11 Ci, from about 11 Ci to about 12 Ci, from about 12 to about 13 Ci, from about 13 to about 14 Ci, or from about 14 to about 15 Ci of $^{64}$Cu. In general, longer bombardment times will yield higher levels of $^{64}$Cu. For example, bombardment times of about 2 h to about 4 h may yield about 2 Ci to about 5 Ci of $^{64}$Cu at EOB, bombardments times of about 6 h may yield about 5 Ci to about 9 Ci of $^{64}$Cu at EOB, and bombardment times of about 12 h may yield about 7 Ci to about 15 Ci of $^{64}$Cu at EOB. In general, the processes disclosed herein may produce from about 1 Ci/h to about 1.5 Ci/h of bombardment with proton beam having an energy of about 12 MeV and a current up to about 225 μA.

(b) Stripping the Bombarded Target

The next step of the process comprises stripping the $^{64}$Ni, $^{64}$Cu, $^{61}$Co, and other metals from the bombarded target. The metals are stripped from the target with a strong acid having a pKa of less than 1. Suitable strong acids include hydrochloric acid, nitric acid, hydrobromic acid, and sulfuric acid. In some embodiments, the bombarded target is stripped with HCl having a molarity from about 6 M to about 12.1 M (concentrated HCl). For example, the bombarded target may be stripped with about 6 M HCl, about 7 M HCl, about 8 M HCl, about 9 M HCl, about 10 M HCl, about 11 M HCl, or about 12.1 M HCl. In specific embodiments, the bombarded target is stripped with about 9 M HCl.

The stripping may comprise adding a volume of the strong acid to a chamber or holding vessel comprising the bombarded target, wherein the target is heated to a temperature from about 65° C. to about 100° C. In particular embodiments, the stripping is conducted at a temperature of about 75° C. After about 3-5 minutes, the acid may be removed and saved as the first strip solution. The target may be contacted with the strong acid several more times, and the resultant solutions combined with the first strip solution. The chamber holding the target then may be rinsed with the strong acid, and the rinse may be combined with the strip solutions to from the final strip solution. In particular embodiments, the bombarded target may be exposed three times with about 3 mL of strong acid (e.g., 9 M HCl) to generate a strip solution of approximately 9 mL.

In some embodiments, the strip solution may be evaporated to dryness or a small volume and the residue may be reconstituted in HCl of the desired molarity (e.g., 9 M) for column chromatography.

In specific embodiments, the stripping comprises contacting the bombarded target with several aliquots of 9 M HCl, at a temperature of about 65° C. to about 100° C., and collecting the aliquots as the strip solution. The chamber holding the bombarded target may be rinsed with 9 M HCl, and the rinse combined with the strip solution.

(c) Purifying $^{64}Cu$ by Ion Exchange Chromatography

The process further comprises isolating the $^{64}Cu$ from the other metals in the strip solution by ion exchange chromatography. In general, the ion exchange chromatography utilizes a strong anion exchange resin. Strong anion exchange resins generally comprise quaternary ammonium groups. For example, a strong anion exchange resin may comprise trialkyl ammonium chloride (e.g., trialkylbenzyl ammonium or trimethylbenzyl ammonium) surface groups or dialkyl 2-hydroxyethyl ammonium chloride (e.g., dimethyl-2-hydroxyethylbenzyl ammonium) surface groups. Examples of suitable strong anion exchange resins comprising trimethylbenzyl ammonium groups include AG® 1-X8 (available from Bio-Rad) and Dowex® 1X8 resin. In specific embodiments, the strong anion exchange resin may be AGR 1-X8, 100-200 mesh, chloride form.

A variety of columns sizes and bed volumes may be used to purify $^{64}Cu$ from the other metals in the strip solution. This process was developed to effectively isolate $^{64}Cu$ generated from about 50 mg of $^{64}Ni$ target material, using about 4.5 g of strong anion exchange resin in a column having an inner diameter of about 1 cm. It is understood that the amount of strong anion exchange resin may range from about 4.0 g to about 5.0 g and the inner diameter of the column may range from about 0.7 cm to about 1.25 cm without departing from the scope of the disclosure. Similarly, the volumes of the eluents passed through the column may vary depending upon the size and volume of the column and/or the amount of $^{64}Ni$ target material. In general, the ion exchange column is equilibrated with HCl (e.g., 9 M HCl) prior to the chromatography process.

(i) Removing $^{64}Ni$

The ion exchange separation process comprises passing the strip solution to the prepared ion exchange column, as well as an additional 1 mL of 9 M HCl used to rinse the holding vessel. The strip solution may be added in multiple smaller aliquots (e.g., 3×3 mL, 2×4.5 mL, etc.) or the strip solution may be added all at once. The Ni in the strip solution does not bind to the strong anion exchange resin and passes through the column, while Cu and Co and other metals bind to the strong anion exchange resin. The column flow through may be collected as a Ni recovery fraction. The column may be rinsed with an additional volume of HCl having the same molarity as that of the strip solution to completely remove any residual Ni from the column. For example, the column may be rinsed with about 10 mL of 9 M HCl. The 10 mL may be added in multiple smaller aliquots (e.g., 5×2 mL, 3×3.333 mL, etc.) or the 10 mL may be added all at once. The column flow through from the rinse may be collected and combined with the original Ni recovery fraction. The combined Ni recovery fraction may be further processed to recover the $^{64}Ni$, which then may be recycled and used for plating additional cyclotron targets. Nickel recovery processes are well known in the art. On average, about 82% of the target $^{64}Ni$ present in the strip solution may be recovered from the Ni recovery fraction. In various embodiments, the percentage of $^{64}Ni$ recovered in the recovery fraction may range from about 40% to about 99% of the starting $^{64}Ni$.

(ii) Removing $^{61}Co$

The ion exchange purification process further comprises adding a volume of HCl having a molarity from about 3 M to about 6 M to the ion exchange column to elute $^{61}Co$. In various embodiments, a volume of 3 M HCl, 4 M HCl, 5 M HCl, or 6 M HCl may be added to the ion exchange column. In specific embodiments, a volume of 4 M HCl may be added to the ion exchange column. For example, about 10 mL of 4 M HCl may be added to the column. The eluent may be added in smaller aliquots (e.g., 5×2 mL, 3×3.33 mL, etc.) or as a bolus. The column eluate may be collected as a waste fraction that mainly comprises $^{61}Co$.

(iii) Isolating $^{64}Cu$

The purification process further comprises adding a volume of HCl having a molarity from about 0.5 M to about 3 M to the ion exchange column to elute the $^{64}Cu$. In certain embodiments, a volume of 0.5 M HCl, 1 M HCl, 2 M HCl, or 3 M HCl may be added to the ion exchange column. In specific embodiments, the $^{64}Cu$ may be eluted from the ion exchange column with a volume of 2 M HCl. For example, about 8 mL to about 20 mL of 2 M HCl may be added to the column. The eluent may be added in smaller aliquots (e.g., 4×2 mL, 4×5 mL, etc.) or as a bolus. The eluate comprising $^{64}Cu$ is collected as the product of the process. On average, about 80% of the $^{64}Cu$ present in the strip solution may be recovered in the eluate comprising $^{64}Cu$. In various embodiments, the percentage of $^{64}Cu$ recovered in the eluate comprising $^{64}Cu$ may range from about 60% to about 100%. The $^{64}Cu$ in the eluate exists as $^{64}CuCl_2$.

The final eluate comprising $^{64}Cu$ may be evaporated to dryness (or to a smaller volume) and the resultant residue may be reconstituted in a volume of HCl having a molarity about 0.001 M to about 1 M. In various embodiments, the residue may be reconstituted in HCl having a molarity from about 0.005 M to about 0.5 M, from about 0.010 M to about 0.2 M, from about 0.025 M to about 0.1 M, or from about 0.04 M to about 0.06 M. In specific embodiments, the residue may be reconstituted in 0.05 M HCl to form a final product comprising $^{64}Cu$.

The $^{64}Cu$ compositions prepared by the processes disclosed herein are described above in section (I).

(iv) Exemplary Ion Exchange Chromatography Purification Process

The 9 M HCl strip solution is passed through the ion exchange column, wherein $^{64}Cu$ and $^{61}Co$ bind to the resin and $^{64}Ni$ flows through the column. The column is rinsed with 9 M HCl to remove residual $^{64}Ni$. The initial column flow through and the 9 M HCL rinse can be combined as the Ni recovery fraction. The column is rinsed with 4 M HCl to elute the $^{61}Co$, which is a waste fraction. Lastly, the $^{64}Cu$ is eluted from the column with 2 M HCl.

Figure 2A:
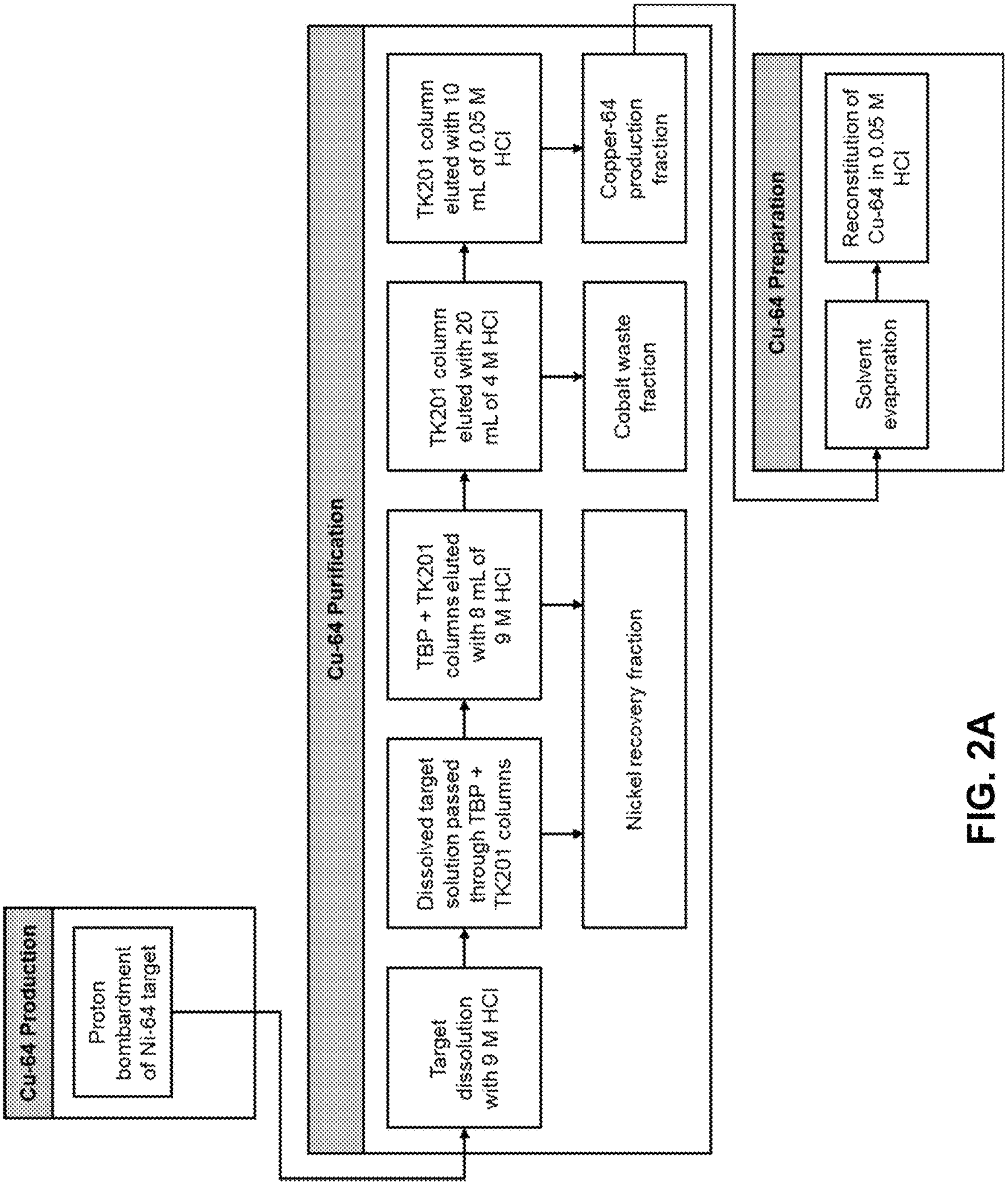
FIGS. 2A, 2B, and 2C present various embodiments of the purification process comprising a combination of extraction chromatography and ion exchange chromatography.
Figure 2B:
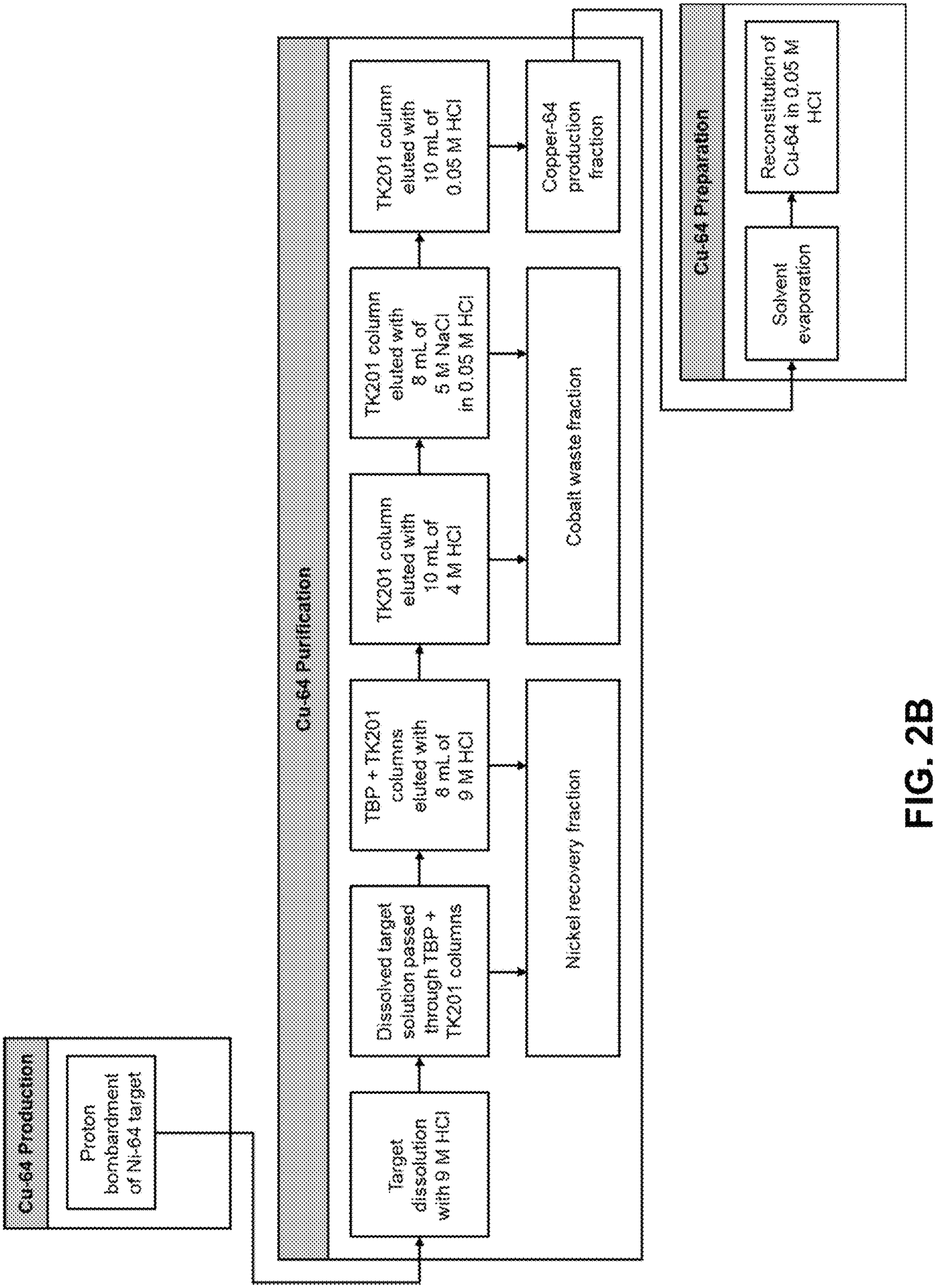
Figure 2C:
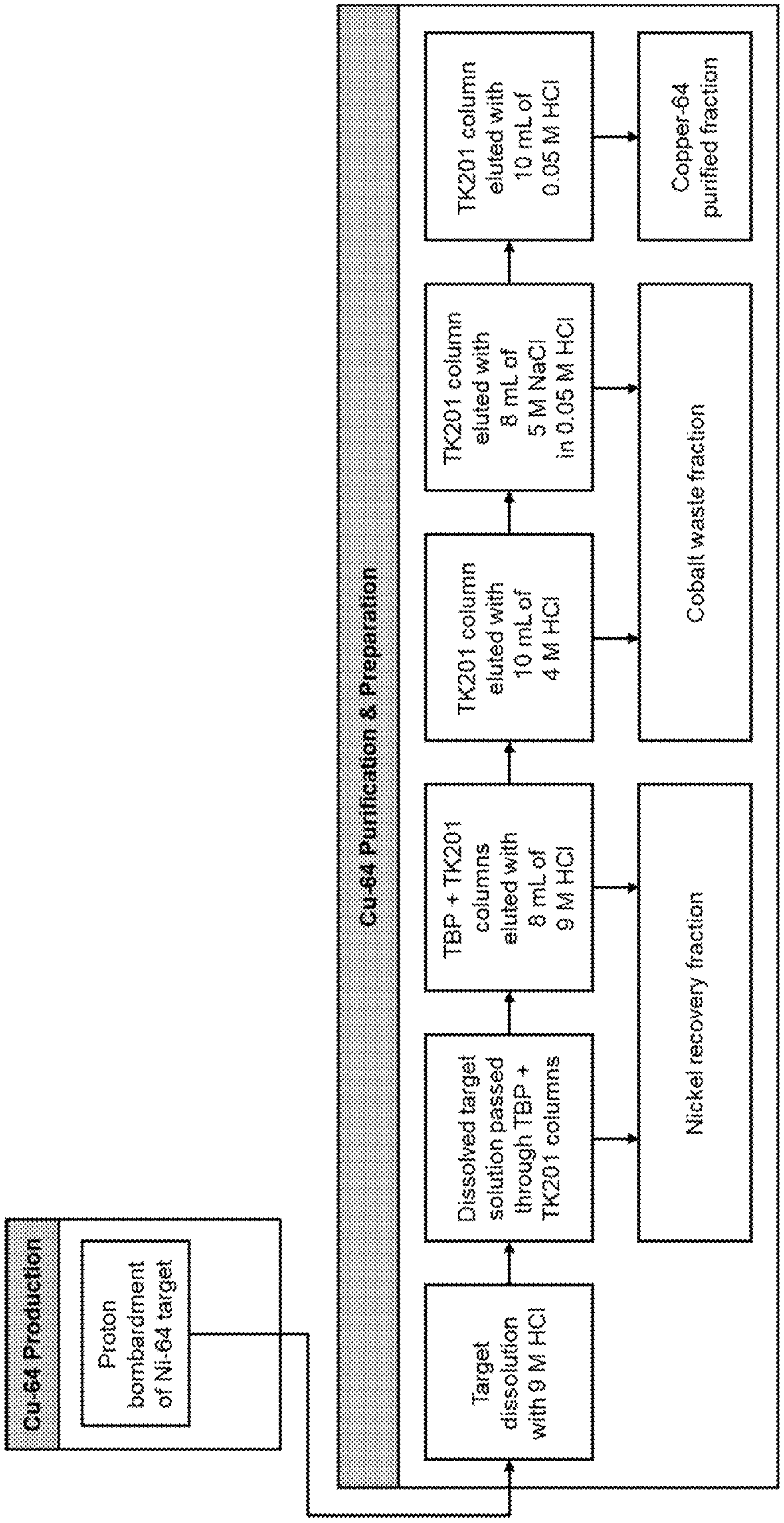

(III) Processes for Producing Copper-64—Purification by Extraction Chromatography and Ion Exchange Chromatography Another aspect of the present disclosure encompasses an additional process for purifying the $^{64}Cu$ from other metals in the strip solution by a combination of extraction chromatography and ion exchange chromatography. The process comprises (a) bombarding a cyclotron target comprising $^{64}Ni$ with a proton beam to generate a bombarded target; (b) stripping the bombarded target with a volume of HCl having a molarity of about 6 M to about 12.1 M to form a strip solution comprising $^{64}Ni$, $^{64}Cu$, $^{61}Co$, and other metals; and (c) purifying the $^{64}Cu$ from the strip solution by chromatography, wherein the chromatography comprises (i) passing the strip solution through a first column comprising an extraction resin connected in series to a second column comprising an ion exchange resin such that the one or more metals (e.g., cationic iron) binds to the extraction resin in the first column, the $^{64}Cu$ and $^{61}Co$ bind to the ion exchange resin in the second column, and $^{64}Ni$ passes through both columns as a first flow-through fraction; (ii) rinsing the first and second columns with a volume of HCl having a molarity of about 6 M to about 12.1 M to remove residual $^{64}Ni$ as a second flow-through fraction; (iii) rinsing the second column with a volume of HCl having a molarity of about 3 M to about 6 M to elute $^{61}Co$ as a first waste fraction; (iv) rinsing the second column with a volume of NaCl having a molarity of about 3 M to 6 M in HCl having a molarity of about 0.01 M to about 3M to elute residual $^{61}Co$ as a second waste fraction or rinsing the second column with an additional volume of HCl having a molarity of about 3 M to about 6 M to elute $^{61}Co$ as a second waste fraction; and (v) adding a volume of HCl having a molarity of about 0.01 M to about 3 M to the second column to elute the $^{64}Cu$ as a product fraction comprising $^{64}Cu$. FIGS. 2A, 2B, and 2C present schematics for several embodiments of the dual chromatography purification process.

(a) Bombarding the Target

Suitable cyclotrons and cyclotron targets are described above in section (II) (a). The cyclotron target may comprise a copper base layer that has been electroplated with gold to a thickness of about 50 μm. The gold-plated cyclotron target then may be plated with enriched $^{64}Ni$. The $^{64}Ni$ may be enriched to about 98%, about 99%, about 99.6%, or about 99.9% $^{64}Ni$. The targeting mass of enriched $^{64}Ni$ may range from about 675 mg to about 825 mg, from about 700 mg to about 800 mg, from about 720 mg to about 780 mg, or about 750 mg. The plating area may range from about 17.3 $cm^2$ to about 28.8 $cm^2$, from about 18.4 $cm^2$ to about 27.6 $cm^2$, from about 20.7 $cm^2$ to about 25.3 $cm^2$, from about 21.8 $cm^2$ to about 24.2 $cm^2$, from about 22.0 $cm^2$ to about 24.0 $cm^2$ or about 23.0 $cm^2$. The plated layer of $^{64}Ni$ may have a thickness from about 21 μm to about 53 μm, from about 26 μm to about 48 μm, from about 32 μm to about 42 μm, or about 37 μm.

In the processes disclosed herein, the $^{64}Ni$ target area is bombarded with low energy protons to produce $^{64}Cu$. In general, the proton beam of the cyclotron is adjusted to have an energy of less than about 20 MeV on the target. In some embodiments, the energy of the proton beam at the target can range from about 5 MeV to about 20 MeV, from about 7 MeV to about 18 MeV, from about 9 MeV to about 16 MeV, from about 10 MeV to about 15 MeV, from about 11 MeV to about 14 MeV, from about 12 MeV to about 13 MeV, or from about 12 MeV to about 14 MeV. In specific embodiments, the actual beam energy at the target is about 12 MeV.

The current of the proton beam may range up to about 408 μA. In some embodiments, the current of the proton beam may range from about 100 μA to about 150 μA, from about 150 μA to about 200 μA, from about 200 μA to about 250 μA, from about 250 μA to about 300 μA, from about 300 μA to about 350 μA, or from about 350 μA to about 410 μA, from about 405 μA to about 410 μA, or about 408 μA. In specific embodiments, the current of the proton beam may range from about 325 μA to about 375 μA, or from about 350 μA to about 408 μA.

The proton beam hits the target area at an angle. In some embodiments, the angle of the proton beam may range from about 1° to about 20°, from about 2° to about 10°, from 2° to about 8°, from about 3° to about 6°, or about 5°. In other embodiments, the angle of the proton beam may be tangential to the target area.

In some embodiments, the beam strike has an elliptic shape with minor and major axes. The minor axes may range from about 25.8 mm to about 34.2 mm, from about 27.9 mm to about 32.1 mm, from about 28.8 mm to about 31.2 mm, or about 30.0 mm. The major axes may range from about 84.4 mm to about 63.6 mm, from about 79.2 mm to about 68.8 mm, from about 77.0 mm to about 71.0 mm, or about 74.0 mm. In certain embodiments, the minor and major axis of the elliptic beam strike may be about 30.0 mm and 74.0 mm, respectively. In some embodiments, the proton beam may strike about 70-80%, about 60-90%, or about 55-95% of the entire target face. In other embodiments, the total area covered by the beam may range from about 14.0 $cm^2$ to about 30.0 $cm^2$, from about 28.0 $cm^2$ to about 16.0 $cm^2$, from about 26.0 $cm^2$ to about 18.0 $cm^2$, or from about 25.0 $cm^2$ to about 20.0 $cm^2$, or 23.0 $cm^2$.

The time of bombardment may range from about 0.5 h to about 24 h. In some embodiments, the time of bombardment may range from 0.5 h to about 8 h, from about 8 h to about 20 h, or from about 20 h to about 24 h. In other embodiments, the bombardment time may range from about 1 h to about 24 h, from about 2 h to about 24 h, from about 4 h to about 24 h, from about 5 h to about 24 h, or about from 5 h to about 23 h. In certain embodiments, the bombardment time may range from about 1 h to about 19 h, from about 2 h to about 19 h, from about 3 h to about 19 h, from about 4 h to about 19 h, or from about 5 h to about 19 h. In other embodiments, the time of bombardment may be less than 19 h, less than 18 h, less than 17.5 h, less than 17 h, less than 16.5 h, less than 16 h, less than 15.5 h, or less than 15 h. In further embodiments, the time of bombardment may be about 8 h, about 9 h, about 10 h, about 11 h, about 12 h, about 13 h, about 14 h, or about 15 h. In specific embodiments, the time of bombardment may range from about 1 h to about 12 h or the time of bombardment may be about 12 h.

In some embodiments, a target comprising about 750 mg $^{64}Ni$ may be bombarded with a proton beam having an energy of about 12 MeV to about 14 MeV and a beam current of about 350 μA to about 408 μA for about 10 h, 12 h, 14 h, 16 h, or 19 h. In specific embodiments, two targets each comprising about 750 mg $^{64}Ni$ may be bombarded simultaneously with a proton beam having an energy of about 12 MeV to about 14 MeV and a beam current, incident on each target, of about 350 μA to about 408 μA for about 10 h, 12 h, 14 h, or 19 h.

The bombarded target may comprise from about 58 Ci to about 80 Ci of $^{64}Cu$ at the end of bombardment (EOB). The bombarded target also comprises unreacted $^{64}Ni$ and $^{61}Co$ that are produced during the bombardment process. In various embodiments, the bombarded target may comprise from about 38 Ci to about 52 Ci, from about 43 Ci to about 59 Ci, from about 48 Ci to about 66 Ci, from about 52 Ci to about 72 Ci, from about 56 Ci to about 77 Ci, or from about 58 Ci to about 80 Ci of $^{64}Cu$. In general, longer bombardment times will yield higher levels of $^{64}Cu$. For example, bombardment times of about 12 h to about 16 h may yield about 43 Ci to about 72 Ci of $^{64}Cu$ at EOB, and bombardments times of about 19 h may yield about 58 Ci to about 80 Ci of $^{64}$Cu at EOB. In general, the processes disclosed herein may produce from about 3.3 Ci/h to about 3.8 Ci/h of bombardment with proton beam having an energy of about 13 MeV and a current of about 350 μA or about 408 μA.

(b) Stripping the Bombarded Target

The next step of the process comprises stripping metals from the bombarded target. The metals are stripped from the target with a strong acid having a pKa of less than 1. Suitable strong acids include hydrochloric acid, nitric acid, hydrobromic acid, and sulfuric acid. In some embodiments, the bombarded target is stripped with HCl having a molarity from about 6 M to about 12.1 M. For example, the bombarded target may be stripped with about 6 M HCl, about 7 M HCl, about 8 M HCl, about 9 M HCl, about 10 M HCl, about 11 M HCl, or about 12.1 M HCl. In specific embodiments, the bombarded target is stripped with about 9 M HCl.

The stripping may comprise adding a volume of the strong acid to a chamber or holding vessel comprising the bombarded target, wherein the target is heated to a temperature from about 65° C. to about 100° C. In particular embodiments, the stripping is conducted at a temperature of about 75° C. After about 3-5 minutes, the acid may be removed and saved as the first strip solution. The target may be contacted with the strong acid several more times, and the resultant solutions combined with the first strip solution. The chamber holding the target then may be rinsed with the strong acid, and the rinse may be combined with the strip solutions to from the final strip solution. In particular embodiments, the bombarded target and the holding chamber may be contacted several times with aliquots (e.g., 5-10 mL) of the strong acid (e.g., HCl) to generate a final strip solution of approximately 20 mL to 40 mL.

In specific embodiments, the stripping comprises contacting the bombarded target with several aliquots of 9 M HCl, at a temperature of about 65° C. to about 100° C., and collecting the aliquots as the strip solution. The chamber holding the bombarded target may be rinsed with 9 M HCl, and the rinse combined with the strip solution. The strip solution comprises $^{64}$Ni, $^{64}$Cu, $^{61}$Co, and can contain other metals (e.g., Fe).

(c) Purifying $^{64}$Cu by Extraction Chromatography and Ion Exchange Chromatography The last step of the process comprises purifying $^{64}$Cu from the other metals in the strip solution by two chromatography columns. The process comprises passing the strip solution through two columns connected in series, the first column comprising an extraction resin and the second column comprising an ion exchange resin.

Extraction chromatography resins generally comprise macroporous polymers that hold an organic complexing compound or extractant within the pore structure of the polymer. Suitable extraction chromatography extractants include tributylphosphate (TBP), carbamoyl-methylphosphine oxide (CMPO), di-(2-ethylhexyl)-phosphoric acid (D2EHPA), and dipentyl pentylphosphonate (DP[PP]). In some embodiments, the extraction chromatography extractant may be a mixture of CMPO and TBP (e.g., TRU resin; TrisKem). In specific embodiments, the extraction chromatography extractant is TBP. An example of a suitable impregnated macroporous polymer (i.e., resin) containing TBP is TrisKem TBP resin. In specific embodiments, the extraction resin may be TBP resin, 100-150 mesh, and in the chloride form.

The ion exchange column comprises a weak anion exchange resin. Weak anion exchange resins generally comprise polystyrene or polyacrylic ester frames that contain a primary, secondary, or tertiary amino group as the functional group. Suitable weak anionic functional groups include diethyl aminoethyl (DEAE) and dimethyl aminoethyl (DMAE). Examples of suitable weak anion exchange resins comprising tertiary ammonium groups include AmberLite™ FPA53 (available from Dupont) and TrisKem TK201 resin. In specific embodiments, the weak anion exchange resin is TK201 resin, 50-100 mesh, and in the chloride form.

A variety of columns sizes and bed volumes may be used to purify $^{64}$Cu from the other metals in the strip solution. This process was developed to effectively isolate $^{64}$Cu generated from about 750 mg of $^{64}$Ni target material, using two distinct columns, containing extraction and weak anion exchange resins, connected in series. The first column comprises about 300 mg of extraction resin in a column having an inner diameter of 0.5 cm. It is understood that the amount of extraction resin may range from about 270 mg to about 330 mg and the inner diameter of the column may range from about 0.4 cm to about 0.6 cm without departing from the scope of the disclosure. The second column uses about 2.7 g of weak anion exchange resin in a column having an inner diameter of about 1 cm. It is understood that the amount of weak anion exchange resin may range from about 2.4 g to about 3.0 g and the inner diameter of the column may range from about 0.7 cm to about 1.25 cm without departing from the scope of the disclosure. Similarly, the volumes of the eluents passed through the column may vary depending upon the size and volume of the column and/or the amount of $^{64}$Ni target material. In general, the columns containing extraction resin and ion exchange resin are equilibrated with HCl (e.g., 9 M HCl) prior to the chromatography process.

(i) Removing Cationic Fe and $^{64}$Ni

The separation process comprises adding the strip solution to the prepared extraction column connected in series to the prepared ion exchange column. In this process, the strip solution volume comprises around 20 mL to around 40 mL. The strip solution may be added in multiple smaller aliquots (e.g., 4×10 mL, 2×10 mL, etc.) or the strip solution may be added all at once. The Fe in the strip solution binds to the extractant (e.g., TBP) in the first column. The Ni in the strip solution does not bind to the chromatographic resins and freely passes through both columns, while Cu and Co and other metals bind to the ion exchange column. The columns flow through volume may be collected as a Ni recovery fraction.

The columns may be rinsed with an additional volume of HCl having the same molarity as that of the strip solution to completely remove any residual Ni from the columns. For example, the columns may be rinsed with about 8 mL to about 10 mL of 9 M HCl. For example, the columns may be rinsed with about 8 mL of 9 M HCl. The volume of HCl may be added in multiple smaller aliquots (e.g., 4×2 mL, 2×4 mL, etc.) or the volume of HCl may be added all at once. The column flow through from the 9 M HCl rinse may be collected and combined with the original Ni recovery fraction. The combined Ni recovery fraction may be further processed to recover the $^{64}$Ni, which then may be recycled and used for plating additional cyclotron targets. Nickel recovery processes are well known in the art. On average, in tracer studies that mimicked a $^{64}$Cu purification, about 98% of the target Ni present in a simulated strip solution may be recovered from the Ni recovery fraction. In various embodiments, the percentage of Ni recovered in the recovery fraction may range from about 40% to about 99% of the starting Ni.

(ii) Removing $^{61}Co$

The separation process further comprises adding a volume of HCl having a molarity from about 3 M to about 6 M to the second column comprising the ion exchange resin to elute $^{61}Co$ (and metals other than Cu). In various embodiments, a volume of 3 M HCl, 4 M HCl, 5 M HCl, or 6 M HCl may be added to the ion exchange column. In specific embodiments, a volume (e.g. from about 10 mL to about 20 mL) of 4 M HCl may be added to the ion exchange column. For example, about 10 mL of 4 M HCl may be added to the ion exchange column. The eluent may be added in smaller aliquots (e.g., 5×2 mL, 3×3.33 mL, etc.) or the eluent may be added all at once. The ion exchange column eluate may be collected as a first waste fraction that mainly comprises $^{61}Co$.

The ion exchange column may be rinsed with an additional volume (e.g., from about 8 mL to about 10 mL) of NaCl having a molarity of about 3 M to 6 M in HCl having a molarity of about 0.01 M to about 3 M to elute residual $^{61}Co$. In specific embodiments, a volume (e.g., 8 mL) of 5 M NaCl in 0.05 M HCl may be added to the ion exchange column. The eluent may be added in smaller aliquots (e.g., 4×2 mL, 2×4 mL, etc.) or the eluent may be added all at once. The ion exchange column eluate from the 5 M NaCl eluent containing $^{61}Co$ may be collected and combined with the first waste fraction containing $^{61}Co$.

Alternatively, the ion exchange column may be rinsed with an additional volume (e.g., from about 8 mL to about 10 mL) of HCl having a molarity from about 3 M to about 6 M to elute residual $^{61}Co$. In specific embodiments, a volume (e.g., 8 mL) of 4 M HCl may be added to the ion exchange column. The eluent may be added in smaller aliquots (e.g., 4×2 mL, 2×4 mL, etc.) or the eluent mL may be added all at once. The ion exchange column eluate from the 5 M HCl eluent containing $^{61}Co$ may be collected and combined with first waste fraction containing $^{61}Co$.

(iii) Isolating $^{64}Cu$

The separation process further comprises adding a volume of HCl having a molarity from about 0.01 M to about 3 M to the ion exchange column to elute the $^{64}Cu$. In certain embodiments, a volume of 0.05 M HCl, 1 M HCl, 2 M HCl, or 3 M HCl may be added to the ion exchange column. In specific embodiments, the $^{64}Cu$ may be eluted from the ion exchange column with a volume of 0.05 M HCl. For example, about 10 mL of 0.05 M HCl may be added to the ion exchange column. The eluent may be added in smaller aliquots (e.g., 5×2 mL, 4×2.5 mL, etc.) or the eluent may be added all at once. The eluate comprising $^{64}Cu$ is collected as the product of the process. On average, in tracer studies that mimicked a $^{64}Cu$ purification, about 89% of the Cu present in a simulated strip solution may be recovered in the eluate comprising Cu. In various embodiments, the percentage of $^{64}Cu$ recovered in the eluate comprising $^{64}Cu$ may range from about 60% to about 100%. The $^{64}Cu$ in the eluate exists as $^{64}CuCl_2$.

The final eluate comprising $^{64}Cu$ may be evaporated to dryness (or to a smaller volume) and the resultant residue may be reconstituted in a volume of HCl having a molarity about 0.001 M to about 1 M. In various embodiments, the residue may be reconstituted in HCl having a molarity from about 0.005 M to about 0.5 M, from about 0.010 M to about 0.2 M, from about 0.025 M to about 0.1 M, or from about 0.04 M to about 0.06 M. In specific embodiments, the residue may be reconstituted in 0.05 M HCl to form a final product comprising $^{64}Cu$.

The $^{64}Cu$ compositions prepared by this process are described above in section (I).

(iv) Exemplary Extraction and Ion Exchange Chromatography Purification Process

The 9 M HCl strip solution is passed through a first column comprising an extraction resin connected in series with a second column comprising a weak anion exchange resin. The Fe in the strip solution binds to the extraction resin in the first column, $^{64}Cu$ and $^{61}Co$ bind to the ion exchange resin in the second column, and $^{64}Ni$ flows through both columns. The first and second columns are rinsed with 9 M HCl to remove residual $^{64}Ni$. The initial column flow through and the 9 M HCL rinse can be combined as the Ni recovery fraction. The ion exchange column is rinsed with 4 M HCl to elute the $^{61}Co$ and then with 5 M NaCl in 0.05 M HCl or additional 4 M HCl to elute residual $^{61}Co$. Lastly, the $^{64}Cu$ is eluted from the ion exchange column with 0.05 M HCl.

(IV) Specific Compositions and Methods of the Disclosure

Accordingly, the present disclosure relates in particular to the following non-limiting compositions and methods.

In a first composition, Composition 1, the present disclosure provides a composition comprising from about 2 Ci to about 15 Ci of copper-64 ($^{64}Cu$) and having a specific activity up to about 3800 mCi $^{64}Cu$/μg Cu.

In another composition, Composition 2, the present disclosure provides a composition comprising from about 2 Ci to about 15 Ci of $^{64}Cu$ at the end of bombardment (EOB) of a single cyclotron run.

In another composition, Composition 3, the present disclosure provides a composition comprising from about 2 Ci to about 5 Ci of $^{64}Cu$ at EOB of a single cyclotron run of about 2 h or about 4 h.

In another composition, Composition 4, the present disclosure provides a composition comprising from about 5 Ci to about 9 Ci of $^{64}Cu$ at EOB of a single cyclotron run of about 6 h.

In another composition, Composition 5, the present disclosure provides a composition comprising up to about 15 Ci of $^{64}Cu$ at EOB of a single cyclotron run of about 12 h In another composition, Composition 6, the present disclosure provides a composition, as provided in any one of Compositions 1 to 5, wherein the composition has a specific activity from about 140 mCi $^{64}Cu$/μg Cu to about 3800 mCi $^{64}Cu$/μg Cu.

In another composition, Composition 7, the present disclosure provides a composition, as provided in any one of Compositions 1 to 6, wherein the composition has a specific activity from about 350 mCi $^{64}Cu$/μg Cu to about 2300 mCi $^{64}Cu$/μg Cu.

In another composition, Composition 8, the present disclosure provides a composition, as provided in any one of Compositions 3 to 7, wherein the single cyclotron run comprises bombarding a nickel-64 target with a beam of protons having an energy of about 12 MeV to about 14 MeV.

In another composition, Composition 9, the present disclosure provides a composition, as provided in any one of Compositions 1 to 8, wherein the composition has a total content of trace metals of less than about 5 parts per million (ppm), the trace metals being cobalt, copper, gold, iron, lead, mercury, nickel, and zinc.

In another composition, Composition 10, the present disclosure provides a composition, as provided in any one of Compositions 1 to 9, wherein the composition comprises a solution of hydrochloric acid (HCl).

In another composition, Composition 11, the present disclosure provides a composition, as provided in Composition 10, wherein the solution comprises about 0.001 M to about 3 M HCl.

In another composition, Composition 12, the present disclosure provides a composition, as provided in Compositions 10 or 11, wherein the solution comprises about 2 M HCl.

In another composition, Composition 13, the present disclosure provides a composition, as provided in any one of Compositions 10 to 12, wherein the solution comprises about 0.05 M HCl.

In another composition, Composition 14, the present disclosure provides a composition, as provided in any one of Compositions 10 to 13, wherein the $^{64}Cu$ exists as $^{64}CuCl_2$.

In another composition, Composition 15, the present disclosure provides a composition, as provided in any one of Compositions 1 to 14, wherein the composition further comprises a chelating agent or a bifunctional chelating agent in which the $^{64}Cu$ is coordinated therein.

In another composition, Composition 16, the present disclosure provides a composition, as provided in Composition 15, wherein the chelating agent or the bifunctional chelating agent is a macrocyclic compound, a bridged macrocyclic compound, a bicyclic compound, or an acyclic compound.

In another composition, Composition 17, the present disclosure provides a composition, as provided in Compositions 15 or 16, wherein the bifunctional chelating agent is DOTA.

In another composition, Composition 18, the present disclosure provides a solution comprising (i) about 2 Ci to about 15 Ci of $^{64}Cu$ that has a specific activity up to about 3800 mCi $^{64}Cu/\mu g$ Cu and (ii) HCl.

In another composition, Composition 19, the present disclosure provides a composition, as provided in Composition 18, wherein the specific activity of the solution is from about 350 mCi $^{64}Cu/\mu g$ Cu to about 2300 mCi $^{64}Cu/\mu g$ Cu.

In another composition, Composition 20, the present disclosure provides a composition, as provided in Compositions 18 or 19, wherein the HCl has a concentration from about 0.001 M to about 3 M.

In another composition, Composition 21, the present disclosure provides a composition, as provided in any one of Compositions 18 to 20, wherein the HCl has a concentration of about 0.5 M.

In another composition, Composition 22, the present disclosure provides a composition, as provided in any one of Compositions 18 to 21, wherein the $^{64}Cu$ exists as $^{64}CuCl_2$.

In another composition, Composition 23, the present disclosure provides a composition, as provided in any one of Compositions 18 to 22, wherein the solution has a total content of trace metals of less than about 5 ppm, the trace metals being cobalt, copper, gold, iron, lead, mercury, nickel, and zinc.

In another composition, Composition 24, the present disclosure provides a composition, as provided in any one of Compositions 18 to 23, wherein the solution further comprises a chelating agent or a bifunctional chelating agent in which the $^{64}Cu$ is coordinated therein.

In another composition, Composition 25, the present disclosure provides a composition, as provided in Composition 25, wherein the chelating agent or the bifunctional chelating agent is a macrocyclic compound, a bridged macrocyclic compound, a bicyclic compound, or an acyclic compound.

In another composition, Composition 26, the present disclosure provides a composition, as provided in Compositions 24 or 25, wherein the bifunctional chelating agent is DOTA.

In another composition, Composition 27, the present disclosure provides a composition for use as a radioactive precursor comprising from 2 Ci to 15 Ci of copper-64 ($^{64}Cu$), and having a specific activity from about 50 mCi $^{64}Cu/\mu g$ Cu up to about 3800 mCi $^{64}Cu/\mu g$ Cu, wherein the composition comprises chemical and radionuclidic purities suitable for positron emission tomography (PET).

In another composition, Composition 28, the present disclosure provides a composition, as provided in Composition 27, wherein the composition has a total content of trace metals of less than about 6 parts per million (ppm), the trace metals being cobalt, copper, gold, iron, lead, mercury, nickel, and zinc.

In another composition, Composition 29, the present disclosure provides a composition, as provided in Composition 27, wherein the composition has a total content of trace metals of less than about 5 parts per million (ppm), the trace metals being cobalt, copper, gold, iron, lead, mercury, nickel, and zinc.

In another composition, Composition 30, the present disclosure provides a composition, as provided in Composition 27, wherein the composition has a total content of trace metals of less than about 3 parts per million (ppm), the trace metals being cobalt, copper, gold, iron, lead, mercury, nickel, and zinc.

In another composition, Composition 31, the present disclosure provides a composition, as provided in Composition 27, wherein the composition has a total content of less than about 6 parts per million (ppm) of copper-67 ($^{67}Cu$).

In another composition, Composition 32, the present disclosure provides a composition, as provided in Composition 27, wherein the composition has a total content of less than about 5 parts per million (ppm) of copper-67 ($^{67}Cu$).

In another composition, Composition 33, the present disclosure provides a composition, as provided in Composition 27, wherein the composition has a total content of less than about 3 parts per million (ppm) of copper-67 ($^{67}Cu$).

In another composition, Composition 34, the present disclosure provides a composition, as provided in Composition 27, wherein the composition has a total content of less than about 1 parts per million (ppm) of copper-67 ($^{67}Cu$).

In another composition, Composition 35, the present disclosure provides a composition, as provided in Composition 27, wherein the composition has a total content of less than about 6 parts per million (ppm) of zinc-68 ($^{68}Zn$).

In another composition, Composition 36, the present disclosure provides a composition, as provided in Composition 27, wherein the composition has a total content of less than about 5 parts per million (ppm) of zinc-68 ($^{68}Zn$).

In another composition, Composition 37, the present disclosure provides a composition, as provided in Composition 27, wherein the composition has a total content of less than about 3 parts per million (ppm) of zinc-68 ($^{68}Zn$).

In another composition, Composition 38, the present disclosure provides a composition, as provided in Composition 27, wherein the composition has a total content of less than about 1 parts per million (ppm) of zinc-68 ($^{68}Zn$).

In another composition, Composition 39, the present disclosure provides a composition, as provided in Composition 27, wherein the composition has a total content of less than about 6 parts per million (ppm) of any atom or isotope with a mass number of 67 or greater.

In another composition, Composition 40, the present disclosure provides a composition, as provided in Composition 27, wherein the composition has a total content of less than about 5 parts per million (ppm) of any atom or isotope with a mass number of 67 or greater.

In another composition, Composition 41, the present disclosure provides a composition, as provided in Composition 27, wherein the composition has a total content of less than about 3 parts per million (ppm) of any atom or isotope with a mass number of 67 or greater.

In another composition, Composition 42, the present disclosure provides a composition, as provided in Composition 27, wherein the composition has a total content of less than about 1 parts per million (ppm) of any atom or isotope with a mass number of 67 or greater.

In another composition, Composition 43, the present disclosure provides a composition, as provided in Composition 27, wherein the composition has a total content of less than about 6 parts per million (ppm) of any atom or isotope with a mass number of 68 or greater.

In another composition, Composition 44, the present disclosure provides a composition, as provided in Composition 27, wherein the composition has a total content of less than about 5 parts per million (ppm) of any atom or isotope with a mass number of 68 or greater.

In another composition, Composition 45, the present disclosure provides a composition, as provided in Composition 27, wherein the composition has a total content of less than about 3 parts per million (ppm) of any atom or isotope with a mass number of 68 or greater.

In another composition, Composition 46, the present disclosure provides a composition, as provided in Composition 27, wherein the composition has a total content of less than about 1 parts per million (ppm) of any atom or isotope with a mass number of 68 or greater.

In another composition, Composition 47, the present disclosure provides a composition, as provided in Composition 27, wherein the composition has an absence of zinc-based target source materials.

In another composition, Composition 48, the present disclosure provides a composition, as provided in Composition 27, wherein the composition has a total content of trace metals of 0 ppm Au, 0 ppm Hg, <0.02 ppm Co, <0.2 ppm Fe, <0.4 ppm Pb, <0.5 ppm Ni, <0.6 ppm Cu, and <1.5 ppm Zn.

In another composition, Composition 49, the present disclosure provides a composition, as provided in Composition 27, wherein the composition comprises a solution of hydrochloric acid (HCl) having a molarity of about 0.001 M to about 3 M.

In another composition, Composition 50, the present disclosure provides a composition, as provided in Composition 27, wherein the $^{64}$Cu exists as $^{64}CuCl_2$.

In another composition, Composition 51, the present disclosure provides a composition, as provided in Composition 27, wherein the composition further comprises a chelating agent or a bifunctional chelating agent in which the $^{64}$Cu is coordinated therein, and the chelating agent or the bifunctional chelating agent is a macrocyclic compound, a bridged macrocyclic compound, a bicyclic compound, or an acyclic compound.

In another composition, Composition 52, the present disclosure provides a composition, as provided in Composition 51, wherein the bifunctional chelating agent is DOTA.

In another composition, Composition 53, the present disclosure provides a composition, as provided in Composition 51, wherein the bifunctional chelating agent is DOTAGA.

In another composition, Composition 54, the present disclosure provides a composition, as provided in Composition 27, wherein the radionuclidic purity of the $^{64}$Cu is greater than 98.5%.

In another composition, Composition 55, the present disclosure provides a composition, as provided in Composition 27, wherein the radionuclidic purity of the $^{64}$Cu is greater than 99.0%.

In another composition, Composition 56, the present disclosure provides a composition, as provided in Composition 27, wherein the radionuclidic purity of the $^{64}$Cu is greater than 99.5%.

In another composition, Composition 57, the present disclosure provides a composition for use as a radioactive precursor comprising from 3 Ci to 15 Ci of copper-64 ($^{64}$Cu), and having a specific activity of about 50 mCi $^{64}$Cu/μg Cu up to about 3800 mCi $^{64}$Cu/μg Cu, wherein the composition comprises chemical and radionuclidic purities suitable for positron emission tomography (PET).

In another composition, Composition 58, the present disclosure provides a composition for use as a radioactive precursor comprising from 4 Ci to 15 Ci of copper-64 ($^{64}$Cu), and having a specific activity of about 100 mCi $^{64}$Cu/μg Cu up to about 3800 mCi $^{64}$Cu/μg Cu, wherein the composition comprises chemical and radionuclidic purities suitable for positron emission tomography (PET).

In another composition, Composition 59, the present disclosure provides a composition comprising copper-64 ($^{64}$Cu) in a single dose vial suitable for administration to a human patient in need thereof, wherein the composition is aliquoted from the composition of Composition 27.

In another composition, Composition 60, the present disclosure provides a composition comprising 35 MBq to 40 MBq of $^{64}$Cu per 1 mL of the composition in a single dose vial suitable for administration to a human patient in need thereof, wherein the composition is aliquoted from the composition of Composition 27.

In another composition, Composition 61, the present disclosure provides a composition comprising 145 MBq to 150 MBq of $^{64}$Cu in a single dose vial suitable for administration to a human patient in need thereof, wherein the composition is aliquoted from the composition of Composition 27.

In another composition, Composition 62, the present disclosure provides a composition comprising $^{64}$Cu in a single dose vial suitable for administration to a human patient in need thereof, wherein the composition is aliquoted from the composition of Composition 57.

In another composition, Composition 63, the present disclosure provides a composition comprising 35 MBq to 40 MBq of $^{64}$Cu per 1 mL of the composition in a single dose vial suitable for administration to a human patient in need thereof, wherein the composition is aliquoted from the composition of Composition 57.

In another composition, Composition 64, the present disclosure provides a composition comprising 145 MBq to 150 MBq of $^{64}$Cu in a single dose vial suitable for administration to a human patient in need thereof, wherein the composition is aliquoted from the composition of Composition 57.

In another composition, Composition 65, the present disclosure provides a composition comprising $^{64}$Cu in a single dose vial suitable for administration to a human patient in need thereof, wherein the composition is aliquoted from the composition of Composition 58.

In another composition, Composition 66, the present disclosure provides a composition comprising 35 MBq to 40 MBq of $^{64}$Cu per 1 mL of the composition in a single dose vial suitable for administration to a human patient in need thereof, wherein the composition is aliquoted from the composition of Composition 58.

In another composition, Composition 67, the present disclosure provides a composition comprising 145 MBq to 150 MBq of $^{64}Cu$ in a single dose vial suitable for administration to a human patient in need thereof, wherein the composition is aliquoted from the composition of Composition 58.

In another composition, Composition 68, the present disclosure provides a composition comprising 145 MBq to 150 MBq of $^{64}Cu$ in a single dose vial suitable for administration to a human patient in need thereof, wherein the composition is aliquoted from the composition of Composition 58.

In another composition, Composition 69, the present disclosure provides a composition, as provided in any one of Compositions 27-68, wherein the composition has a total content of less than about 6 parts per million (ppm) of $^{67}Cu$.

In another composition, Composition 70, the present disclosure provides a composition, as provided in any one of Compositions 27-69, wherein the composition has a total content of less than about 5 parts per million (ppm) of $^{67}Cu$.

In another composition, Composition 71, the present disclosure provides a composition, as provided in any one of Compositions 27-70, wherein the composition has a total content of less than about 3 parts per million (ppm) of $^{67}Cu$.

In another composition, Composition 72, the present disclosure provides a composition, as provided in any one of Compositions 27-71, wherein the composition has a total content of less than about 1 parts per million (ppm) of $^{67}Cu$.

In another composition, Composition 73, the present disclosure provides a composition, as provided in any one of Compositions 27-72, wherein the composition has a total content of less than about 6 parts per million (ppm) of $^{68}Zn$.

In another composition, Composition 74, the present disclosure provides a composition, as provided in any one of Compositions 27-73, wherein the composition has a total content of less than about 5 parts per million (ppm) of $^{68}Zn$.

In another composition, Composition 75, the present disclosure provides a composition, as provided in any one of Compositions 27-74, wherein the composition has a total content of less than about 3 parts per million (ppm) of $^{68}Zn$.

In another composition, Composition 76, the present disclosure provides a composition, as provided in any one of Compositions 27-75, wherein the composition has a total content of less than about 1 parts per million (ppm) of $^{68}Zn$.

In another composition, Composition 77, the present disclosure provides a composition, as provided in any one of Compositions 27-76, wherein the composition has a total content of less than about 6 parts per million (ppm) of any atom or isotope with a mass number of 67 or greater.

In another composition, Composition 78, the present disclosure provides a composition, as provided in any one of Compositions 27-77, wherein the composition has a total content of less than about 5 parts per million (ppm) of any atom or isotope with a mass number of 67 or greater.

In another composition, Composition 79, the present disclosure provides a composition, as provided in any one of Compositions 27-78, wherein the composition has a total content of less than about 3 parts per million (ppm) of any atom or isotope with a mass number of 67 or greater.

In another composition, Composition 80, the present disclosure provides a composition, as provided in any one of Compositions 27-79, wherein the composition has a total content of less than about 1 parts per million (ppm) of any atom or isotope with a mass number of 67 or greater.

In another composition, Composition 81, the present disclosure provides a composition, as provided in any one of Compositions 27-80, wherein the composition has a total content of less than about 6 parts per million (ppm) of any atom or isotope with a mass number of 68 or greater.

In another composition, Composition 82, the present disclosure provides a composition, as provided in any one of Compositions 27-81, wherein the composition has a total content of less than about 5 parts per million (ppm) of any atom or isotope with a mass number of 68 or greater.

In another composition, Composition 83, the present disclosure provides a composition, as provided in any one of Compositions 27-82, wherein the composition has a total content of less than about 3 parts per million (ppm) of any atom or isotope with a mass number of 68 or greater.

In another composition, Composition 84, the present disclosure provides a composition, as provided in any one of Compositions 27-83, wherein the composition has a total content of less than about 1 parts per million (ppm) of any atom or isotope with a mass number of 68 or greater.

In another composition, Composition 85, the present disclosure provides a composition, as provided in any one of Compositions 27-84, wherein the composition has an absence of zinc-based target source materials.

In a first process, Process 1, the present disclosure provides a process for preparing copper-64 ($^{64}Cu$) from nickel-64 ($^{64}Ni$), the process comprising (a) bombarding a cyclotron target comprising $^{64}Ni$ with a proton beam to generate a bombarded target; (b) stripping the bombarded target with a volume of hydrochloric acid (HCl) having a molarity of about 6 M to about 12.1 M to form a strip solution comprising $^{64}Ni$ and $^{64}Cu$; and (c) purifying the $^{64}Cu$ from the strip solution by ion exchange chromatography comprising: (i) passing the strip solution through a column comprising an ion exchange resin such that $^{64}Cu$ binds to the ion exchange resin and $^{64}Ni$ passes through the column as a flow-through; (ii) rinsing the column with a volume of HCl having a molarity of about 3 M to about 6 M; and (iii) adding a volume of HCl having a molarity of about 0.5 M to about 3 M to the column to elute the $^{64}Cu$ from the ion exchange resin and collecting an eluate comprising $^{64}Cu$.

In another process, Process 2, the present disclosure provides a process, as provided in Process 1, wherein the cyclotron target comprises about 50 mg of $^{64}Ni$ plated in an area of about 4.0 $cm^2$.

In another process, Process 3, the present disclosure provides a process, as provided in Processes 1 or 2, wherein the proton beam has an energy of about 10 MeV to about 14 MeV and a current of about 100 μA to about 250 μA.

In another process, Process 4, the present disclosure provides a process, as provided in any one of Processes 1 to 3, wherein the proton beam has an energy of about 12 MeV and a current up to about 225 μA.

In another process, Process 5, the present disclosure provides a process, as provided in any one of Processes 1 to 4, wherein the bombarding proceeds for about 1 h to about 6 h.

In another process, Process 6, the present disclosure provides a process, as provided in any one of Processes 1 to 5, wherein after the bombarding, the bombarded target comprises from about 2 Ci to about 12 Ci of $^{64}Cu$ at the end of bombardment (EOB).

In another process, Process 7, the present disclosure provides a process, as provided in Process 6, wherein after about 2 h to about 4 h of bombarding, the bombarded target comprises from about 2 Ci to about 5 Ci of $^{64}Cu$ at EOB.

In another process, Process 8, the present disclosure provides a process, as provided in Process 6, wherein after about 6 h of bombarding, the bombarded target comprises from about 5 Ci to about 9 Ci of $^{64}Cu$ at EOB.

In another process, Process 9, the present disclosure provides a process, as provided in any one of Processes 1 to 8, wherein the stripping of the bombarded target is conducted at a temperature of about 65° C. to about 100° C.

In another process, Process 10, the present disclosure provides a process, as provided in any one of Processes 1 to 9, wherein the stripping comprises contacting the bombarded target three times with an aliquot of 9 M HCl for about 3-5 minutes each time, and collecting the aliquots as the strip solution.

In another process, Process 11, the present disclosure provides a process, as provided in any one of Processes 1 to 10, wherein the bombarded target is rinsed with an additional aliquot of 9 M HCl, which is then added to the strip solution.

In another process, Process 12, the present disclosure provides a process, as provided in any one of Processes 1 to 11, wherein the ion exchange resin is a strong anion exchange resin comprising trimethylbenzyl ammonium chloride groups.

In another process, Process 13, the present disclosure provides a process, as provided in any one of Processes 1 to 12, wherein the flow-through from passing the strip solution through the column is collected as a $^{64}$Ni recovery fraction.

In another process, Process 14, the present disclosure provides a process, as provided in any one of Processes 1 to 13, wherein after passing the strip solution through the column, a further volume of 9 M HCl is added to the column and its flow-through is combined with the $^{64}$Ni recovery fraction.

In another process, Process 15, the present disclosure provides a process, as provided in Process 14, wherein an average of about 82% of the target $^{64}$Ni is recovered in the $^{64}$Ni recovery fraction.

In another process, Process 16, the present disclosure provides a process, as provided in any one of Processes 1 to 15, wherein the rinsing comprises adding 4 M HCl to the column to elute cobalt, which is collected as a waste fraction.

In another process, Process 17, the present disclosure provides a process, as provided in any one of Processes 1 to 16, wherein the $^{64}$Cu is eluted form the column with 2 M HCl.

In another process, Process 18, the present disclosure provides a process, as provided in any one of Processes 1 to 17, wherein an average of about 80% of the $^{64}$Cu present in the strip solution is recovered in the eluate comprising $^{64}$Cu.

In another process, Process 19, the present disclosure provides a process, as provided in any one of Processes 1 to 18, wherein the eluate comprising $^{64}$Cu is evaporated to dryness and reconstituted in 0.05 M HCl, thereby forming a final product comprising $^{64}$Cu.

In another process, Process 20, the present disclosure provides a process, as provided in Process 19, wherein the final product comprising $^{64}$Cu comprises from about 2 Ci to about 12 Ci of $^{64}$Cu.

In another process, Process 21, the present disclosure provides a process, as provided in Processes 19 or 20, wherein the final product comprising $^{64}$Cu has a specific activity up to about 3800 mCi $^{64}$Cu/μg Cu.

In another process, Process 22, the present disclosure provides a process, as provided in any one of Processes 19 to 21, wherein the final product comprising $^{64}$Cu has a specific activity from about 350 mCi $^{64}$Cu/μg Cu to about 2300 mCi $^{64}$Cu/μg Cu.

In another process, Process 23, the present disclosure provides a process, as provided in any one of Processes 19 to 22, wherein the final product comprising $^{64}$Cu has a total content of trace metals of less than about 5 ppm, the trace metals being cobalt, copper, gold, iron, lead, mercury, nickel, and zinc.

In another process, Process 24, the present disclosure provides an additional process for preparing copper-64 ($^{64}$Cu) from nickel-64 ($^{64}$Ni), in which the $^{64}$Cu is purified by a combination of extraction chromatography and ion exchange chromatography. The process comprises (a) bombarding a cyclotron target comprising $^{64}$Ni with a proton beam to generate a bombarded target; (b) stripping the bombarded target with a volume of HCl having a molarity of about 6 M to about 12.1 M to form a strip solution comprising $^{64}$Ni, $^{64}$Cu, $^{61}$Co, and one or more trace metals; and (c) purifying the $^{64}$Cu from the strip solution by chromatography, wherein the chromatography comprises (i) passing the strip solution through a first column comprising an extraction resin connected in series to a second column comprising an ion exchange resin, such that the one or more trace metals binds to the extraction resin in the first column, $^{64}$Cu and $^{61}$Co bind to the ion exchange resin in the second column, and $^{64}$Ni passes through both columns as a first flow-through fraction. The process further comprises (ii) rinsing the first and second columns with a volume of HCl having a molarity of about 6 M to about 12.1 M to remove residual $^{64}$Ni as a second flow-through fraction; (iii) rinsing the second column with a volume of HCl having a molarity of about 3 M to about 6 M to elute $^{61}$Co as a first waste fraction; (iv) rinsing the second column with a volume of NaCl having a molarity of about 3 M to 6 M in HCl having a molarity of about 0.01 M to about 3 M to elute residual $^{61}$Co as a second waste fraction or rinsing the second column with an additional volume of HCl having a molarity of about 3 M to about 6 M to elute $^{61}$Co as a second waste fraction; and (v) adding a volume of HCl having a molarity of about 0.01 M to about 3 M to the second column to elute the $^{64}$Cu as a product fraction comprising $^{64}$Cu.

In another process, Process 25, the present disclosure provides a process, as provided in Process 24, wherein the cyclotron target at (a) comprises about 750 mg of $^{64}$Ni plated in an area of about 23.0 $cm^2$.

In another process, Process 26, the present disclosure provides a process, as provided in Processes 24 or 25, wherein the proton beam at (a) has an energy of about 10 MeV to about 15 MeV and a current of about 350 μA to about 408 μA.

In another process, Process 27, the present disclosure provides a process, as provided in any one of Processes 24 to 26, wherein the proton beam at (a) has an energy of about 13 MeV and a current of about 350 μA to about 408 μA.

In another process, Process 28, the present disclosure provides a process, as provided in any one of Processes 24 to 27, wherein the bombardment (a) proceeds for about 12 h to about 24 h, and the bombarded target comprises from about 46 Ci to about 82 Ci of $^{64}$Cu at the end of bombardment (EOB).

In another process, Process 29, the present disclosure provides a process, as provided in Processes 28, wherein after about 16 h to about 20 h of bombarding at (a), the bombarded target comprises from about 56 Ci to about 75 Ci of $^{64}$Cu at EOB.

In another process, Process 30, the present disclosure provides a process, as provided in Processes 28, wherein after about 19 h of bombarding at (a), the bombarded target comprises from about 62 Ci to about 73 Ci of $^{64}$Cu at EOB.

In another process, Process 31, the present disclosure provides a process, as provided in any one of Processes 24 to 30, wherein the stripping at (b) comprises contacting the bombarded target with 9 M HCl, and the stripping at (b) is conducted at a temperature of about 65° C. to about 100° C.

In another process, Process 32, the present disclosure provides a process, as provided in any one of Processes 24 to 31, wherein the extraction resin in the first column at (c) (i) comprises tributylphosphate as a functional group, and the ion exchange resin in the second column at (c) (i) comprises a tertiary amine as a functional group.

In another process, Process 33, the present disclosure provides a process, as provided in any one of Processes 24 to 32, wherein the rinsing at (c) (ii) comprises 9 M HCl.

In another process, Process 34, the present disclosure provides a process, as provided in any one of Processes 24 to 33, wherein the first and second flow-through fractions are combined as a $^{64}$Ni recovery fraction.

In another process, Process 35, the present disclosure provides a process, as provided in Process 34, wherein an average of about 98% of the target $^{64}$Ni is recovered in the $^{64}$Ni recovery fraction.

In another process, Process 36, the present disclosure provides a process, as provided in any one of Processes 24 to 35, wherein the rinsing at (c) (iii) comprises 4 M HCl, and the rising at (c) (iv) comprises 5 M NaCl in 0.05 M HCl or additional 4 M HCl.

In another process, Process 37, the present disclosure provides a process, as provided in any one of Processes 24 to 36, wherein the $^{64}$Cu is eluted at (c) (v) with 0.05 M HCl.

In another process, Process 38, the present disclosure provides a process, as provided in any one of Processes 24 to 37, wherein an average of about 89% of the $^{64}$Cu present in the strip solution is recovered in the product fraction comprising $^{64}$Cu.

In another process, Process 39, the present disclosure provides a process, as provided in any one of Processes 24 to 38, wherein the product fraction comprising $^{64}$Cu comprises from about 2 Ci to about 15 Ci of $^{64}$Cu and has a specific activity up to about 3800 mCi $^{64}$Cu/μg Cu.

In another process, Process 40, the present disclosure provides a process, as provided in any one of Processes 24 to 39, wherein the product fraction comprising $^{64}$Cu has a total content of trace metals of less than about 5 ppm, the trace metals being cobalt, copper, gold, iron, lead, mercury, nickel, and zinc.

Definitions

The features, structures, steps, or characteristics disclosed herein in connection with one embodiment may be combined in any suitable manner in one or more alternative embodiments.

The indefinite articles "a" and "an," as used herein in the specification and in the claims, unless clearly indicated to the contrary, should be understood to mean "at least one."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

The term "carrier," as used herein refers to an inactive material deliberately added to a specified radioactive substance to ensure that the radioactivity will behave normally in all subsequent chemical and physical processes.

The term "non-carrier added" refers to a preparation of a radioactive isotope which is 'free' from stable isotopes of the element in question. More precisely, a preparation of a radioactive isotope of high specific activity to which no isotopic carrier was intentionally added and which was not produced by irradiation of a stable isotope of the same element.

EXAMPLES

The following examples illustrate various non-limiting embodiments of the present disclosure.

Example 1: Separation of Metals Via Ion Exchange Chromatography

According to the literature, a bombarded Ni target typically is dissolved in 6 M hydrochloric acid (HCl) and the resulting solution is purified via anion exchange chromatography. After the nickel has completely eluted from the column, the eluent is changed to low molarity HCl (often ≤0.5 M) or water and the copper is collected as it is released from column. However, $^{64}$Cu prepared this way typically contains some $^{61}$Co, as Co elutes from the resin in ≤4 M HCl. Thus, to obtain better separation of Co and Cu, a trial separation of various metals was performed using solutions of 6 M, 4 M, and 2 M HCl to elute Ni, Co, and Cu, respectively.

A solution containing 5.0 mg/mL Ni and 25 μg/mL each of Co, Cu, Fe, Zn, Hg and Pb in 6 M HCl was prepared to mimic an un-purified mixture. A glass Econo-column (0.7 cm×20 cm) was dry-packed with 4.5 g of AG 1-X8 resin (16 cm bed height, 6 mL bed volume). The resin was pre-treated by washing the column with 30 mL of Chelex-treated $H_2O$ followed by 30 mL of 6 M HCl. This rinse cycle was repeated once more so that the final wash was with 6 M HCl. The columns were gravity drained and each wash was considered complete once droplet formation ceased.

The column was loaded with 10 mL of the metal solution (50 mg Ni, 250 μg each added metal) and the flow through was collected as 2×5 mL fractions (load fraction). The column was eluted with the following: 5×2 mL aliquots of 6 M HCl (6 M fraction), 5×2 mL aliquots of 4 M HCl (4 M fraction), 5×2 mL aliquots of 2 M HCl (2 M fraction), and 1×5 mL aliquot of 0.5 M HCl (0.5 M fraction). Each eluate and an aliquot of the initial unpurified mixture were analyzed by Inductively Coupled Plasma Optical Emission Spectroscopy (ICP-OES). Table 1 presents the amount of metal present in each fraction as a percentage of what was present in the initial unpurified mixture.

TABLE 1

Percent of metal in each fraction.

| | Load | 6M | 4M | 2M | 0.5M |
|---|---|---|---|---|---|
| Ni | 89.5 | 31.9 | 0.0 | 0.0 | 0.0 |
| Co | 36.5 | 46.5 | 16.7 | 0.0 | 0.0 |
| Cu | 0.0 | 0.0 | 9.6 | 80.6 | 0.1 |
| Fe | 0.0 | 0.0 | 0.0 | 10.7 | 40.7 |

TABLE 1-continued

| Percent of metal in each fraction. | | | | | |
|---|---|---|---|---|---|
| | Load | 6M | 4M | 2M | 0.5M |
| Hg | 0.0 | 0.0 | 0.0 | 0.0 | 0.0 |
| Pb | 0.4 | 7.2 | 44.0 | 20.0 | 6.4 |
| Zn | 36.9 | 13.1 | 0.0 | 0.0 | 0.0 |

As expected, Ni was present in the load fraction and the 6 M HCl fraction. The majority of Cu was present in 2 M HCl fraction, with a small amount (9.6%) present in the 4 M HCl fraction. Co was observed in the load, 6 M HCl, and 4 M HCl fractions, with no co-elution with Cu in the 2 M HCl fraction. Thus, there was good separation of Ni and Co from Cu, with 80.6% of the total Cu collected in the 2 M HCl faction with no co-elution of either Ni or Co. The only other tested metals present in the 2 M HCl fraction were small percentages of Pb and Fe.

Example 2: Varying Molarity of Starting Acid

To determine whether early breakthrough of Co could be reduced, as well as Pb breakthrough in the 2 M HCl fraction, the molarity of the starting acid was increased to 9 M HCl.

A solution containing 5.0 mg/mL Ni and 25 μg/mL each of Co, Cu, Fe, Zn, Hg and Pb in 9 M HCl was prepared. A column comprising 4.5 g of AG 1-X8 resin was prepared described above in Example 1. The column resin was pre-treated with 30 mL of Chelex-treated $H_2O$ followed by 30 mL of 9 M HCl. This rinse cycle was repeated once more so that the final wash was with 9 M HCl. The prepped column was loaded with 10 mL of the Ni solution (50 mg Ni, 250 μg each added metal) and collected as 2×5 mL fractions. The column then was eluted, and fractions collected with the following: 5×2 mL fractions of 9 M HCl, 5×2 mL fractions of 4 M HCl, 5×2 mL fractions of 2 M HCl, and 1×5 mL of 0.5 M HCl. Samples of the eluates and the initial unpurified mixture were analyzed via ICP-OES. These data are presented in Table 2.

TABLE 2

| Percent of metal in each fraction. | | | | | |
|---|---|---|---|---|---|
| | Load | 9M HCl | 4M HCl | 2M HCl | 0.5M HCl |
| Ni | 78.7 | 27.6 | 0 | 0 | 0 |
| Co | 3.1 | 0.9 | 94.0 | 0.3 | 0 |
| Cu | 0 | 0 | 2.1 | 93.0 | 0.1 |
| Fe | 0 | 0 | 0 | 9.0 | 41.4 |
| Hg | 0 | 0 | 0 | 0 | 0 |
| Pb | 10.6 | 83.2 | 4.7 | 0.1 | 0 |
| Zn | 36.8 | 12.9 | 0 | 0 | 0 |

The use of 9 M HCl as the starting acid concentration improved the overall separation process by shifting the elution profiles of Co and Pb. The majority of Co was eluted in the 4 M HCl fraction (rather than the earlier fractions), and the majority of Pb was eluted in the load and 9 M HCl fractions (rather than the 4 M HCl fraction). The 2 M HCl fraction contained mainly Cu with a low percentage of Fe and trace amounts of Co and Pb.

Example 3: Adjusting a CS-30 Cyclotron to Reduce Proton Beam Energy

Copper-64 may be produced by bombarding enriched nickel-64 with low energy protons (e.g., less than 14 MeV). At higher beam energies, the production of $^{61}$Co and stable $^{63}$Cu increases and $^{64}$Cu production decreases, therefore $^{64}$Cu production from $^{64}$Ni via the (p,n) reaction is best performed with 12 MeV protons.

It has been generally assumed that CS-30 cyclotrons were not suitable for $^{64}$Cu production because they may accelerate a proton beam up to about 30 MeV. It is generally accepted that a cyclotron cannot attain a beam energy lower than half of its maximum energy. Thus, the lowest energy attainable in CS-30 cyclotrons, in theory, is about 15 MeV.

Figure 3:
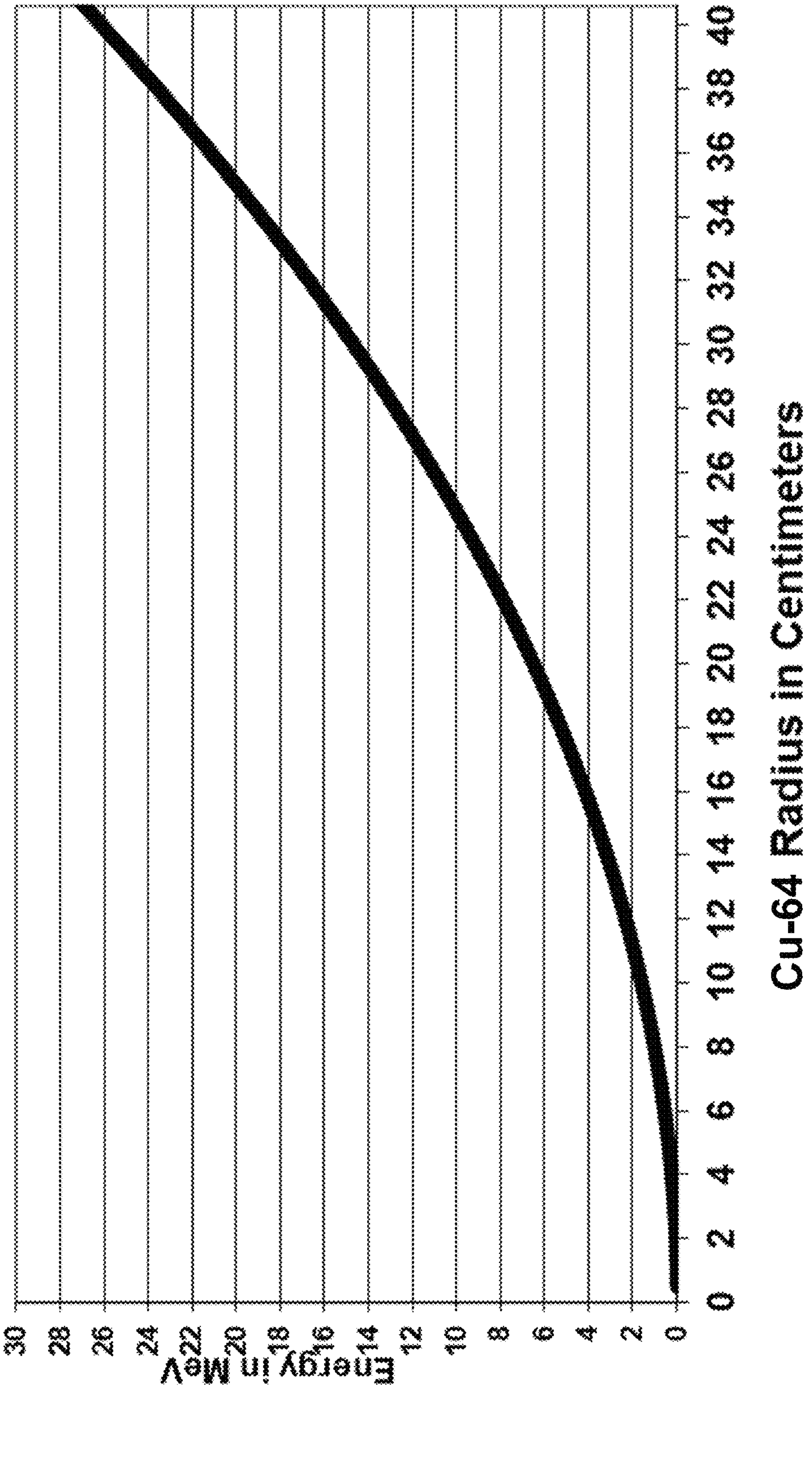
FIG. 3 is a plot of proton energy as a function of proton beam radius.

The output energy of a cyclotron is given by the equation $E=(rqB)^2/2$ m, where E is the particle energy, r is the radius at which the targets are inserted, q is the charge on the particle of interest, B is the magnetic field, and m is the mass of the particle being accelerated. Since protons are being accelerated, the mass and charge are $1.672\times10^{-27}$ kg, and $1.602\times10^{-19}$ C, respectively. The magnetic field used in CS-30 cyclotrons is 1.847 T. FIG. 3 shows the proton energy as a function of the proton beam radius. This plot predicts a target radius of about 27.9 cm to attain a beam energy of about 12 MeV.

Thus, in order to produce the desired proton beam energy of 12 MeV, the location of the target was adjusted in the cyclotron so that the proton beam would strike the target at the smaller radius of about 27.9 cm.

Initial beam strikes with CS-30 curved targets showed that the proton beam went too far along one edge of the target, all of the way to the end, with no beam on the majority of the target face, completely missing the opposite edge. Only about 25% of the entire target face had beam on it, and half of that was on an unusable edge. With this arrangement, too much of the beam would be lost, and hence it is unsuitable. This was remedied by substituting a flat target for the curved one. Using a flat target allowed the beam to strike about one-fifth of the total target area (e.g., about one-fifth from the end of the target). The total area covered by the beam was 4 $cm^2$. The beam strike from the flat target was acceptable. Tuning parameters of the CS-30 were determined to give the best beam strike at the new radius of 27.9 cm. Thus, by using a flat target, the target radius was reduced, and the energy of the proton beam could be reduced to about 12 MeV.

Example 4: Target Bombardments of Enriched Nickel-64

A CS-30 cyclotron adjusted as described above in Example 3 was used to produce $^{64}$Cu. For this, about 50 mg of $^{64}$Ni (~99% isotopically enriched) was electroplated on a CS-30 cyclotron flat target comprising a copper base layer that had been electroplated with gold to a thickness of about 50 μm. The plated area was about 4.0 $cm^2$. The target was bombarded with a beam energy of about 12 MeV, a beam current of 200 μA or 225 μA, and bombardment time of 1 to 6 h. The target was stripped with 9 M HCl and the resultant solution was analyzed by HPGe gamma spectroscopy to determine $^{64}$Cu yield at the end of bombardment (EOB). Table 3 shows results of preliminary runs.

TABLE 3

| Yield of Test Runs. | | | |
|---|---|---|---|
| Run | Beam Current | Bombardment Time | $^{64}$Cu Activity, calibrated to EOB |
| 1 | 200 μA | 1 h | 674.1 mCi |
| 2 | 200 μA | 6 h | 6,102 mCi |

TABLE 3-continued

| Yield of Test Runs. | | | |
|---|---|---|---|
| Run | Beam Current | Bombardment Time | $^{64}Cu$ Activity, calibrated to EOB |
| 3 | 225 μA | 1 h | 1,424.8 mCi |
| 4 | 225 μA | 6 h | 6,900.1 mCi |

Example 5: Purification of Copper-64 from a Bombarded Nickel-64 Target

Flat CS-30 cyclotron targets that had been electroplated with 50 μm of gold, were plated with enriched $^{64}Ni$, targeting a mass of about 50 mg and a plated area of 4.0 $cm^2$. The target was bombarded for 1 to 6 h with a beam energy of about 12 MeV and beam current of approximately 200 μA or 225 μA. The bombarded target was stripped using three 3.0 mL aliquots of 9 M HCl. During this time, the target stripping cell was heated to 75° C., and each aliquot was held 3-5 minutes. After the hold time, the 3-mL aliquot was removed and placed in a holding vessel. The aliquots were collected together as one, approximately 9 mL strip solution.

The $^{64}Cu$ was isolated and purified by anion exchange chromatography essentially as described above in Example 2. For this, a glass ion-exchange column (inner diameter=1.0 cm, length=20 cm) was nitric acid washed, rinsed with high resistivity water, and packed with 4.5 g AG 1-X8 resin (chloride form), 100 to 200 mesh (8 cm bed height, 6 mL bed volume). The column resin was pre-treated by washing twice with Chelex-treated 18.2 MΩ·cm resistivity water followed by 9 M HCl.

The 9-mL strip solution was loaded onto a pre-treated ion-exchange column along with an additional 1 mL of 9 M HCl that was used to rinse the vessel holding the strip solution. The 10-mL load volume was eluted from the column by gravity at ~1 mL per minute as the load fraction. Gravity filtration was used for all the solutions that passed through the column. The column was then rinsed with another 10 mL of 9 M HCl and the eluate was combined with the load fraction. The combined fractions (approximately 20 mL) comprised the $^{64}Ni$ recovery fraction. After the $^{64}Ni$ recovery fraction was collected from the column, 10 mL of 4 M HCl was added to the column. The eluate comprising cobalt was collected separately as a waste fraction. After the 4 M HCl fraction was collected from the column, 8 mL of 2 M HCl was added to the column. The 2 M HCl eluate collected in a separate vial and contained the $^{64}Cu$ product. The 2 M HCl eluate was evaporated to dryness and reconstituted in 0.05 M HCl to a target radioactive concentration of approximately 1.25 Ci/mL.

Aliquots of the strip solution and the eluates were analysed by gamma spectroscopy and/or with a dose calibrator to determine $^{64}Cu$ activity, and via ICP-OES to determine metallic content. The yield of $^{64}Cu$ at EOB for 15 runs ranged from 674 mCi (1 h bombardment at 200 μA) to 8,706 mCi (6 h bombardment at 200 μA). The average yield of $^{64}Cu$ at EOB for 8 runs that had a bombardment time of 6 h and beam current of 200-225 μA was 67132.6 mCi (s.d.=1189.1). The average recovery of $^{64}Cu$ in the 2 M HCl eluate (relative to the strip solution) for the 15 runs was about 80% (s.d.=20%). After reconstituting the $^{64}Cu$ in 0.05 M HCl, the resulting specific activity of the $^{64}CuCl_2$ averaged 965.8 mCi $^{64}Cu$/μg Cu (s.d.=658) at EOB when measured by the dose calibrator, and 1,724.2 mCi $^{64}Cu$/μg Cu (s.d.=750) at EOB when measured by the HPGe detector. The Cu content was determined via ICP-OES. Further analysis revealed no statistically significant difference between the dose calibrator and the HPGe detector. The dose calibrator method was preferred because it was more straightforward to use during manufacturing. The average recovery of $^{64}Ni$ (in the $^{64}Ni$ recovery fraction) from the 15 processed targets was about 82%.

Presented below is a detailed analysis of the purified product from three representative runs. For these runs, the target was bombarded for 6 h with a beam energy of approximately 12 MeV and beam current of 200 or 22 μA. Total activity was measured with a dose calibrator calibrated for $^{64}Cu$. Table 4 shows the activity of $^{64}Cu$ collected after the purification process. Table 4 also shows the purification process yields as amount of $^{64}Cu$ per total activity of the strip solution (as determined by dose calibrator).

TABLE 4

| Recovery of $^{64}Cu$ During Purification | | | |
|---|---|---|---|
| | Batch 1 | Batch 2 | Batch 3 |
| Strip Solution (mCi) | 9,872.0 | 10,625 | 10,798 |
| 2M HCl Eluate (mCi) | 6,154.4 | 8,385 | 8,760 |
| % $^{64}Cu$ recovery | 62.3% | 78.9% | 81.1% |

Table 5 presents the levels of trace metals in the 2 M HCl eluate.

TABLE 5

| TraceMetal Analysis in 2M HCl Eluate | | | |
|---|---|---|---|
| | Batch 1 | Batch 2 | Batch 3 |
| Au (μg/mL) | 0 | 0 | 0 |
| Co (μg/mL) | 0 | 0 | 0.047 |
| Cu (μg/mL) | 0.343 | 0.745 | 0.673 |
| Fe (μg/mL) | 0.102 | 0.117 | 0.261 |
| Hg (μg/mL) | 0 | 0 | 0 |
| Ni (μg/mL) | 0.434 | 0.403 | 0.484 |
| Pb (μg/mL) | 0.031 | 0.031 | 0.886 |
| Zn (μg/mL) | 0.114 | 1.899 | 2.448 |

Table 6 presents the specific activity of the $^{64}Cu$ product in the 0.05 M HCl solution.

TABLE 6

| Specific Activity of $^{64}Cu$ in 0.05M HCl Solution | | | |
|---|---|---|---|
| | Batch 1 | Batch 2 | Batch 3 |
| $^{64}Cu$ activity (i)mC | 4,041.1 | 7,650.0 | 8,109.0 |
| Cu mass (μg) | 2.0 | 8.2 | 5.7 |
| Specific Activity (mCi $^{64}Cu$/μg Cu) | 2,010.5 | 937.6 | 1,425.2 |

Example 6. Separation of Metals Via Extraction and Ion Exchange Chromatography A trial separation of various metals was performed using a combination of extraction chromatography and ion exchange chromatography to more effectively separate Cu from masses of Ni up to 750 mg, Co, Fe, and other transition metals.

A polyethylene (PE) column (0.7 cm×20 cm) was vacuum-packed using 20 mL of 0.05 M HCl with 2.7 g of TK201 resin (about 5 cm to 6 cm bed height, about 1 mL to 2 mL bed volume). A PE frit was securely placed atop the packed resin bed. The packed PE column, containing TK201 resin, was rinsed with 20 ml of 0.05 M HCl under vacuum. The packed PE column was capped and stored at 4.4° C.

The pre-packed PE column containing 2.7 g of TK201 resin, stored in 0.05 M HCl at 4.4° C., and a 2 mL PE column containing 300 mg of TBP resin were pre-treated by washing each column with 10 mL of high-resistivity water (HRW) followed by 10 mL of 9 M HCl. The HRW and 9 M HCl were passed through each column at a flow-rate of 1 mL/min using a syringe pump. Each wash was considered complete once droplet formation ceased.

A solution containing 25.0 mg/mL Ni, 20.4 μg/mL Co, 8.6 μg/mL Cu, 8.1 μg/mL Fe, and 10.3 μg/mL Pb was prepared in 9 M HCl to simulate a bombarded target stripping solution.

The PE columns, connected in series, were loaded at a flow-rate of 1 mL/min using a syringe pump with 30 mL of the metal solution (746 mg Ni, 259 μg Cu, 611 μg Co, 244 μg Fe, 309 μg Pb) and the flow through was collected as a single 30 mL fraction (load fraction). The two columns were eluted with 2×4 mL aliquots of 9 M HCl (9 M fraction) and the flow through was collected. The ion exchange column was then eluted with the following: 2×5 mL aliquots of 4 M HCl (4 M fraction), 2×4 mL aliquots of 5 M NaCl in 0.05 M HCl (5 M NaCl fraction), and 2×5 mL aliquot of 0.05 M HCl (0.05 M fraction). Each eluate and an aliquot of the initial mixture were analyzed by Inductively Coupled Plasma Optical Emission Spectroscopy (ICP-OES). Table 7 presents the amount of metal present in each fraction as a percentage of the starting amount in the simulated stripping solution mixture.

TABLE 7

Percentages of Various Metals in Each Fraction

| Element | Load | 9M HCl | 4M HCl | 5M NaCl | 0.05M HCl |
|---|---|---|---|---|---|
| Co | 53.5 | 7.0 | 21.6 | 11.4 | n.d.* |
| Cu | n.d. | n.d. | n.d. | n.d. | 86.5 |
| Ni | 88.3 | 10.1 | 0.03 | n.d. | n.d. |
| Fe | n.d. | n.d. | n.d. | n.d. | n.d. |
| Pb | 75.4 | 11.4 | 0 | 0 | 0 |

*n.d. = not detected or below the limits of detection

As expected, Ni was present in the load fraction and the 9 M HCl rinse fraction (98.4%). The Cu was measured only in the 0.05 M HCl fraction (86.5%). Co was observed in the load, 9 M HCl, 4 M HCl, and 5 M NaCl fractions, with no co-elution of Cu in the 0.05 M HCl fraction. Thus, there was good separation of Ni and Co from Cu, with 86.5% of the total Cu collected in the 0.05 M HCl faction with no co-elution of either Ni or Co.

What is claimed is:

1. A composition suitable for administration to a human patient in need thereof comprising copper-64 ($^{64}$Cu) at a specific activity from 50 mCi $^{64}$Cu/μg Cu to 3850 mCi $^{64}$Cu/μg Cu, wherein the composition comprises chemical and radionuclidic purities suitable for positron emission tomography (PET).

2. The composition of claim 1, wherein the radionuclidic purity of the $^{64}$Cu is greater than 98.0%.

3. The composition of claim 1, wherein the radionuclidic purity of the $^{64}$Cu is greater than 99.0%.

4. The composition of claim 1, wherein the composition comprises from 36 MBq to about 38 MBq of $^{64}$Cu per 1 mL.

5. The composition of claim 1, wherein the composition has a total content of less than 6 parts per million (ppm) of copper-67 ($^{67}$Cu).

6. The composition of claim 1, wherein the composition has a total content of less than 5 parts per million (ppm) of $^{67}$Cu.

7. The composition of claim 1, wherein the composition has a total content of less than 3 parts per million (ppm) of $^{67}$Cu.

8. The composition of claim 1, wherein the composition has a total content of less than 1 parts per million (ppm) of $^{67}$Cu.

9. The composition of claim 1, wherein the composition has a total content of less than about 6 parts per million (ppm) of zinc-68 ($^{68}$Zn).

10. The composition of claim 1, wherein the composition has a total content of less than about 5 parts per million (ppm) of $^{68}$Zn.

11. The composition of claim 1, wherein the composition has a total content of less than about 3 parts per million (ppm) of $^{68}$Zn.

12. The composition of claim 1, wherein the composition has a total content of less than about 1 parts per million (ppm) of $^{68}$Zn.

13. The composition of claim 1, wherein the composition has a total content of less than about 6 parts per million (ppm) of any atom or isotope with a mass number of 67 or greater.

14. The composition of claim 1, wherein the composition has a total content of less than about 5 parts per million (ppm) of any atom or isotope with a mass number of 67 or greater.

15. The composition of claim 1, wherein the composition has a total content of less than about 3 parts per million (ppm) of any atom or isotope with a mass number of 67 or greater.

16. The composition of claim 1, wherein the composition has a total content of less than about 1 parts per million (ppm) of any atom or isotope with a mass number of 67 or greater.

17. The composition of claim 1, wherein the composition has a total content of less than about 6 parts per million (ppm) of any atom or isotope with a mass number of 68 or greater.

18. The composition of claim 1, wherein the composition has a total content of less than about 5 parts per million (ppm) of any atom or isotope with a mass number of 68 or greater.

19. The composition of claim 1, wherein the composition has a total content of less than about 3 parts per million (ppm) of any atom or isotope with a mass number of 68 or greater.

20. The composition of claim 1, wherein the composition has a total content of less than about 1 parts per million (ppm) of any atom or isotope with a mass number of 68 or greater.

21. The composition of claim 1, wherein the composition is isolated from a composition comprising from 5 Ci to 15 Ci of $^{64}$Cu.

22. The composition of claim 1, wherein the composition is isolated from a composition comprising from 3 Ci to 15 Ci of $^{64}$Cu.

23. The composition of claim 1, wherein the composition is provided in a single dose vial.

24. A composition suitable for administration to a human patient in need thereof comprising copper-64 ($^{64}$Cu) at a specific activity from 50 mCi to 3850 mCi $^{64}$Cu/μg Cu and DOTATATE, and wherein the composition comprises chemical and radionuclidic purities suitable for positron emission tomography (PET), and wherein the radionuclidic purity of the $^{64}Cu$ is greater than 95.0%.

25. The composition of claim 24, wherein the radionuclidic purity of the $^{64}Cu$ is greater than 95.0% 98.0%.

26. The composition of claim 24, wherein the radionuclidic purity of the $^{64}Cu$ is greater than 99.0%.

27. The composition of claim 24, wherein the composition comprises from about 35 MBq to about 40 MBq of $^{64}Cu$ DOTATATE per 1 mL.

28. The composition of claim 24, wherein the composition has a total content of less than 1 parts per million (ppm) of $^{67}Cu$.

29. A composition suitable for administration to a human patient in need thereof comprising at a specific activity from 25 mCi $^{64}Cu$/µg Cu to 3850 mCi $^{64}Cu$/µg Cu, wherein the composition comprises chemical and radionuclidic purities suitable for positron emission tomography (PET), and wherein the composition further comprises DOTA or DOTAGA.

30. A composition suitable for administration to a human patient in need thereof comprising from 35 MBq to 40 MBq of copper-64 ($^{64}Cu$) per mL of the composition at a specific activity from 50 mCi $^{64}Cu$/µg Cu to 3850 mCi $^{64}Cu$/µg Cu, wherein the composition comprises chemical and radionuclidic purities suitable for positron emission tomography (PET).

* * * * *